US008554299B2

(12) United States Patent
Sinderby et al.

(10) Patent No.: US 8,554,299 B2
(45) Date of Patent: Oct. 8, 2013

(54) ELECTRODE FOR PHYSIOLOGICAL SIGNAL MEASUREMENTS AND METHOD FOR MAKING SAME

(75) Inventors: Christer Sinderby, Toronto (CA); Norm Comtois, West Hill (CA); Göran Rydgren, Bunkeflostrand (SE); Tord Lindner, Täby (SE)

(73) Assignee: Maquet Critical Care AB, Solna (SE)

( * ) Notice: Subject to any disclaimer, the term of this patent is extended or adjusted under 35 U.S.C. 154(b) by 0 days.

(21) Appl. No.: 13/474,283

(22) Filed: May 17, 2012

(65) Prior Publication Data

US 2012/0226125 A1    Sep. 6, 2012

Related U.S. Application Data

(63) Continuation of application No. 11/813,559, filed as application No. PCT/CA2006/000049 on Jan. 12, 2006, now Pat. No. 8,204,570.

(60) Provisional application No. 60/643,104, filed on Jan. 12, 2005, provisional application No. 60/697,381, filed on Jul. 8, 2005.

(51) Int. Cl.
*A61B 5/042*    (2006.01)

(52) U.S. Cl.
USPC ............................ 600/380; 600/393; 600/509

(58) Field of Classification Search
USPC ................. 600/372, 373, 380, 393, 509, 381; 29/825
See application file for complete search history.

(56) References Cited

U.S. PATENT DOCUMENTS

| 3,485,937 | A | * | 12/1969 | Caveney | 174/101 |
|---|---|---|---|---|---|
| 4,574,807 | A | * | 3/1986 | Hewson et al. | 607/27 |
| 4,592,372 | A | * | 6/1986 | Beranek | 607/119 |
| 4,911,148 | A | * | 3/1990 | Sosnowski et al. | 600/136 |
| 5,433,742 | A | * | 7/1995 | Willis | 607/122 |
| 5,458,631 | A | * | 10/1995 | Xavier | 607/117 |
| 5,484,407 | A | * | 1/1996 | Osypka | 604/95.04 |
| 6,120,476 | A | * | 9/2000 | Fung et al. | 604/95.04 |
| 6,363,286 | B1 | * | 3/2002 | Zhu et al. | 607/120 |
| 6,584,347 | B1 | * | 6/2003 | Sinderby | 600/546 |
| 6,932,816 | B2 | * | 8/2005 | Phan | 606/49 |
| 6,939,350 | B2 | * | 9/2005 | Phan | 606/49 |
| 7,000,784 | B2 | * | 2/2006 | Canty et al. | 211/26 |
| 7,615,003 | B2 | * | 11/2009 | Stefanchik et al. | 600/104 |
| 8,204,570 | B2 | * | 6/2012 | Sinderby et al. | 600/373 |
| 2003/0130564 | A1 | * | 7/2003 | Martone et al. | 600/121 |
| 2003/0158547 | A1 | * | 8/2003 | Phan | 606/41 |
| 2005/0097737 | A1 | * | 5/2005 | Webster et al. | 29/854 |
| 2006/0206109 | A1 | * | 9/2006 | Swanson | 606/41 |

* cited by examiner

*Primary Examiner* — Lee S Cohen
*Assistant Examiner* — Erin M Cardinal
(74) *Attorney, Agent, or Firm* — Fay Kaplun & Marcin, LLP

(57) ABSTRACT

The present invention is concerned with an electrode and electrode catheter using thin metallic threads or wires, for example, microwires having diameters as low as $10^{-6}$ to $10^{-4}$ meters or less. The embodiments allow for the efficient mounting of at least one electrode on a catheter, resulting in the creation of a flexible ring-microelectrode that is suitable for, amongst other things, the detection of myoelectrical activity in a patient's muscle, such as the diaphragm or other inspiratory-related muscle.

19 Claims, 28 Drawing Sheets

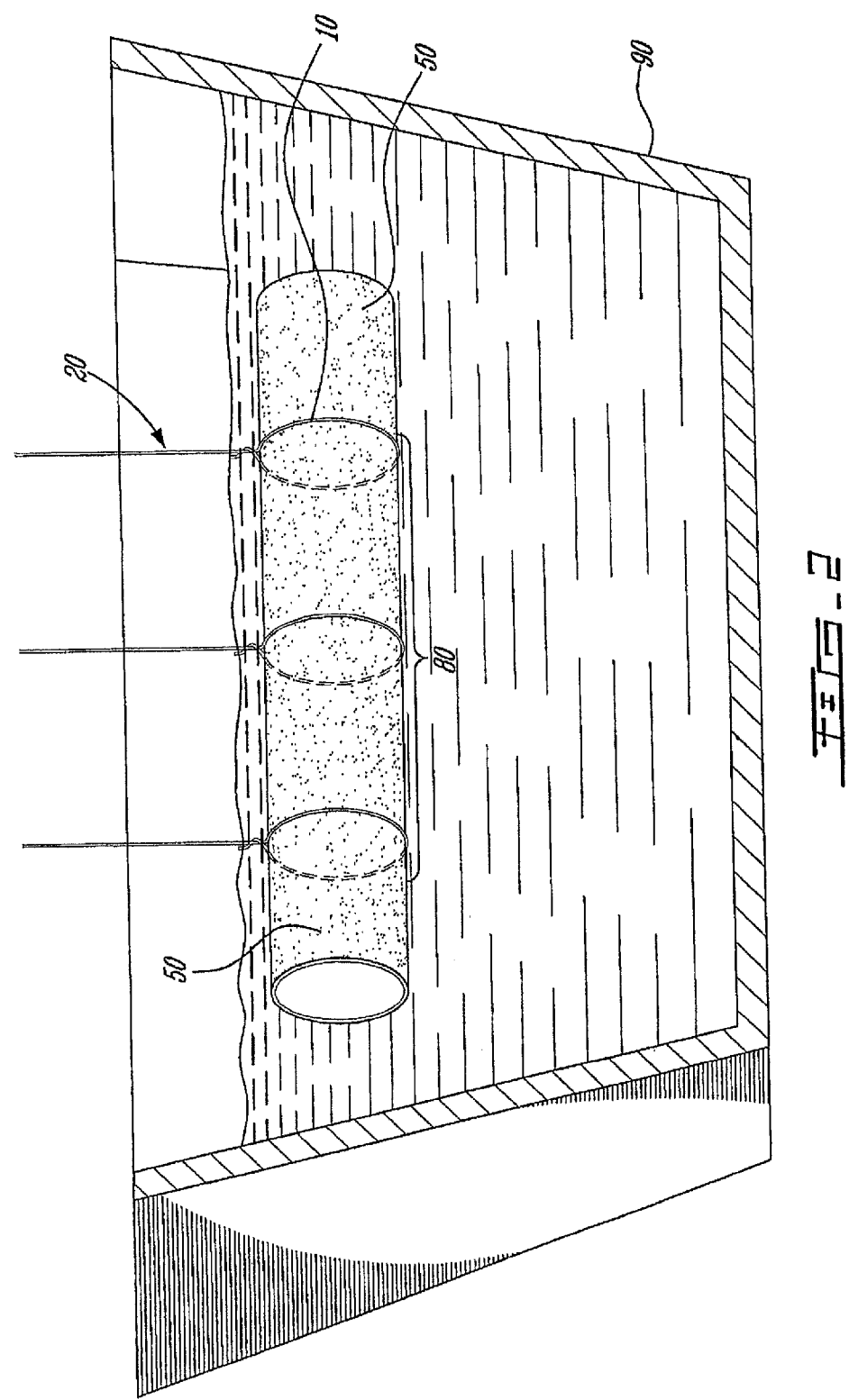

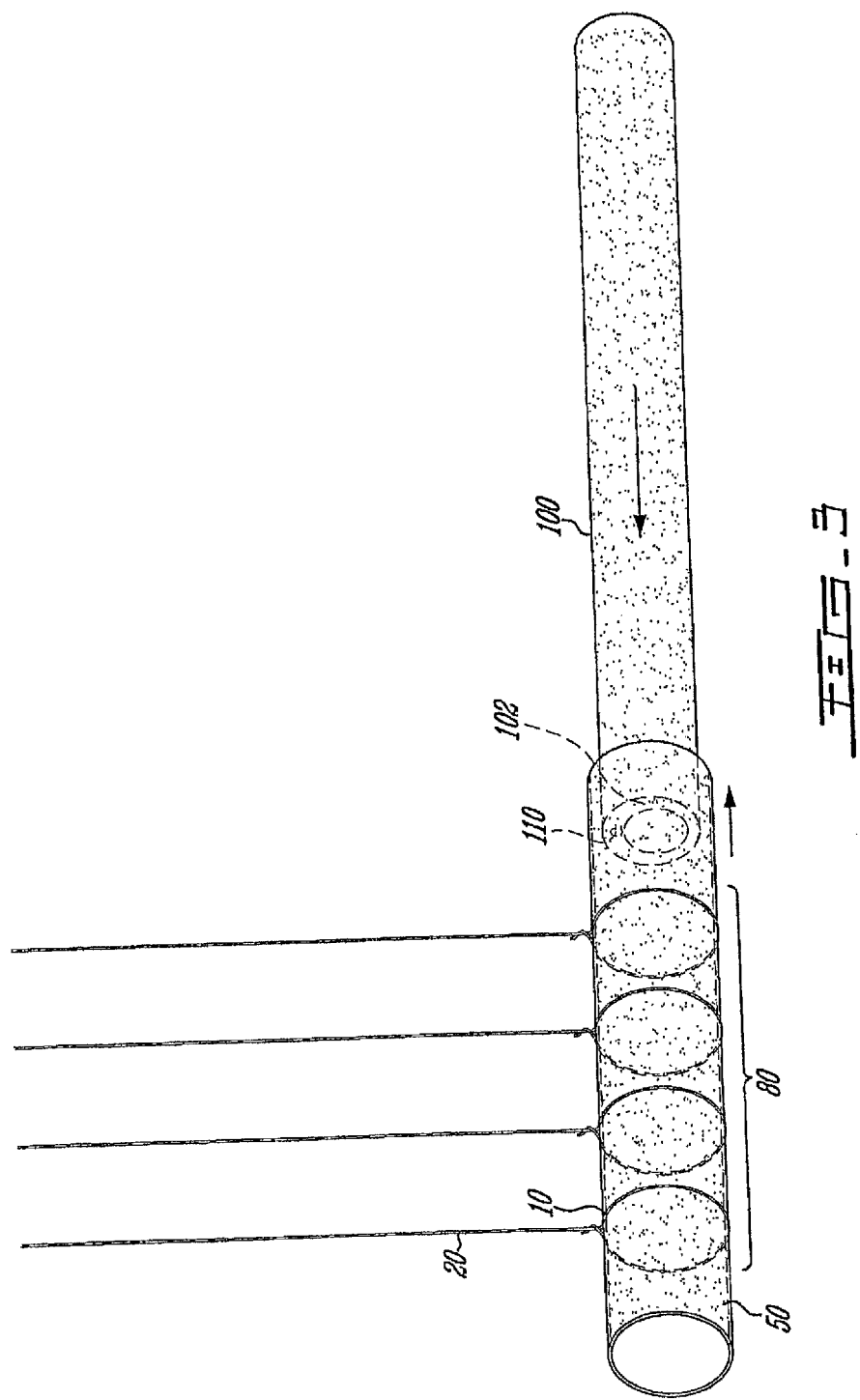

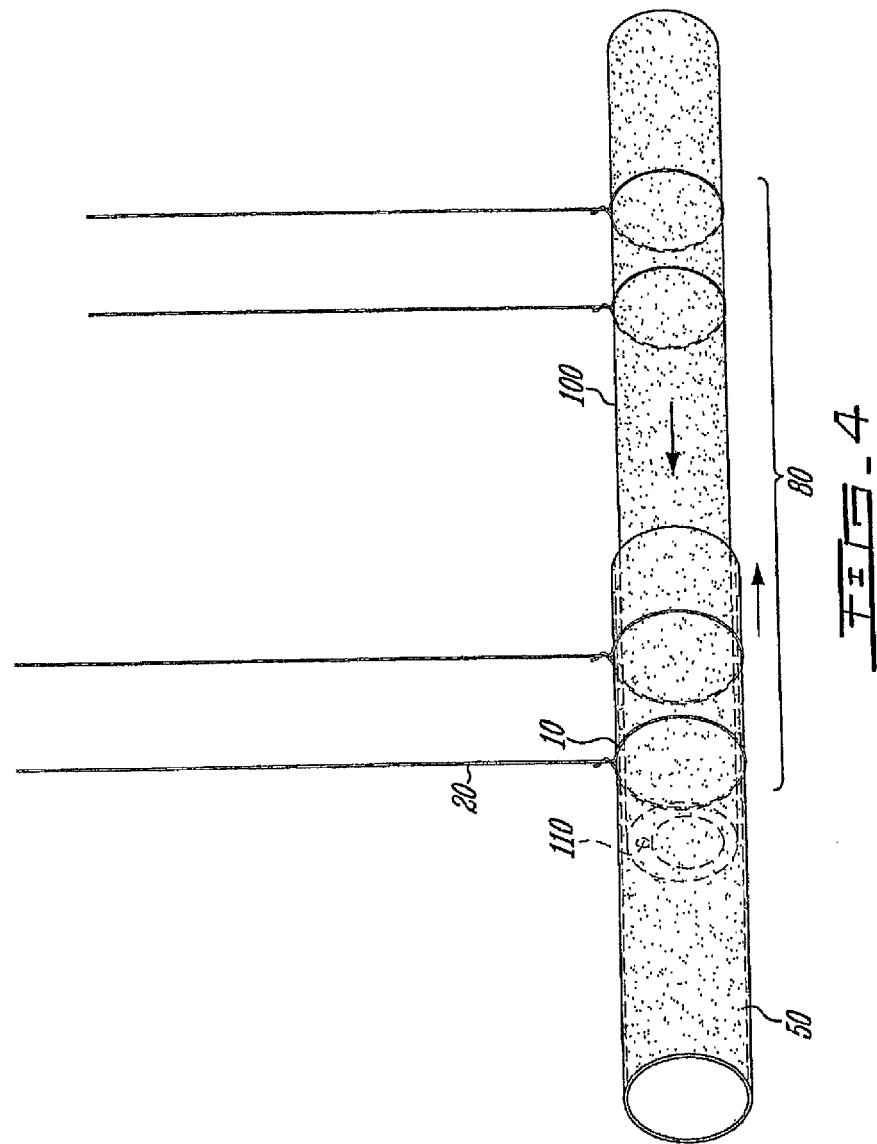

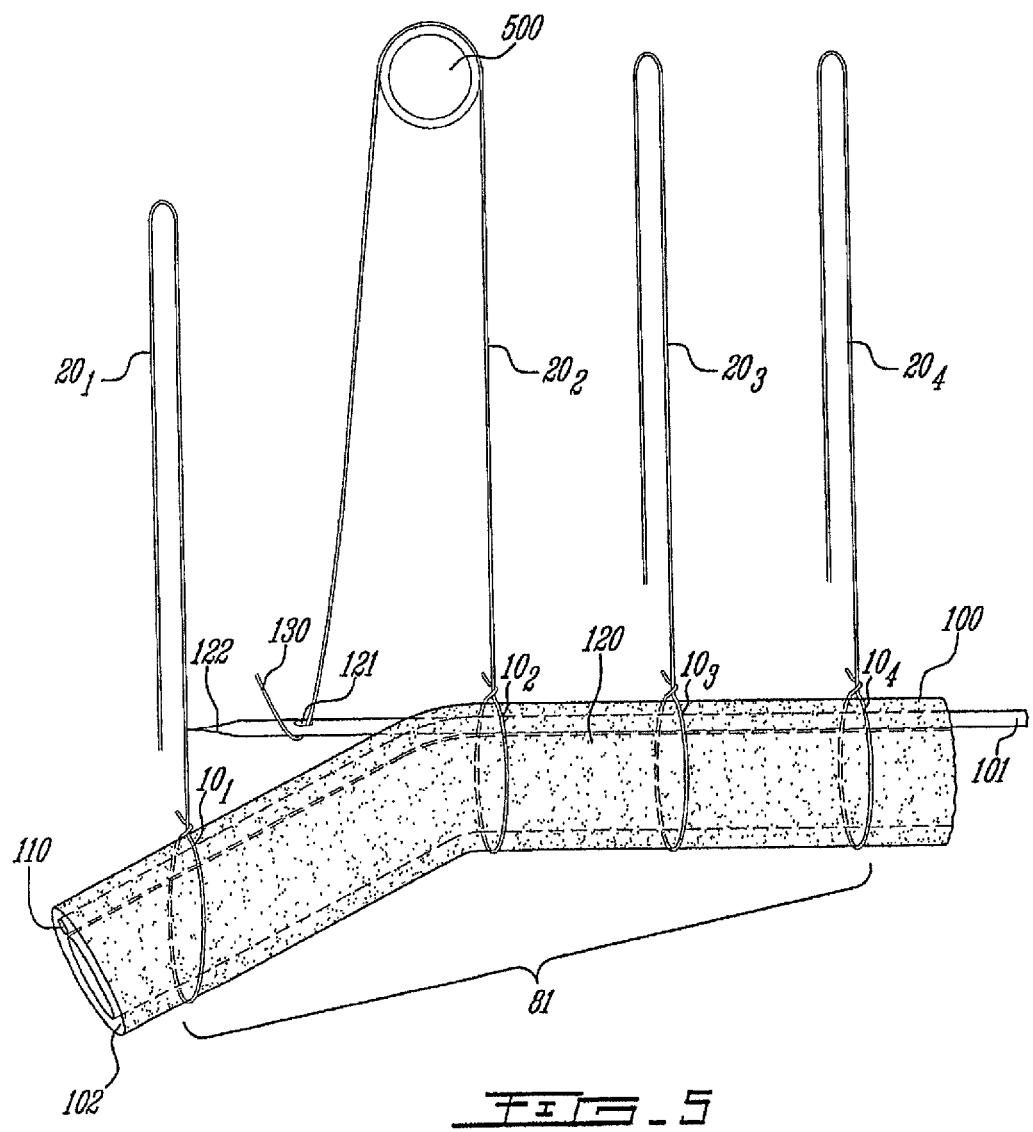
FIG_5

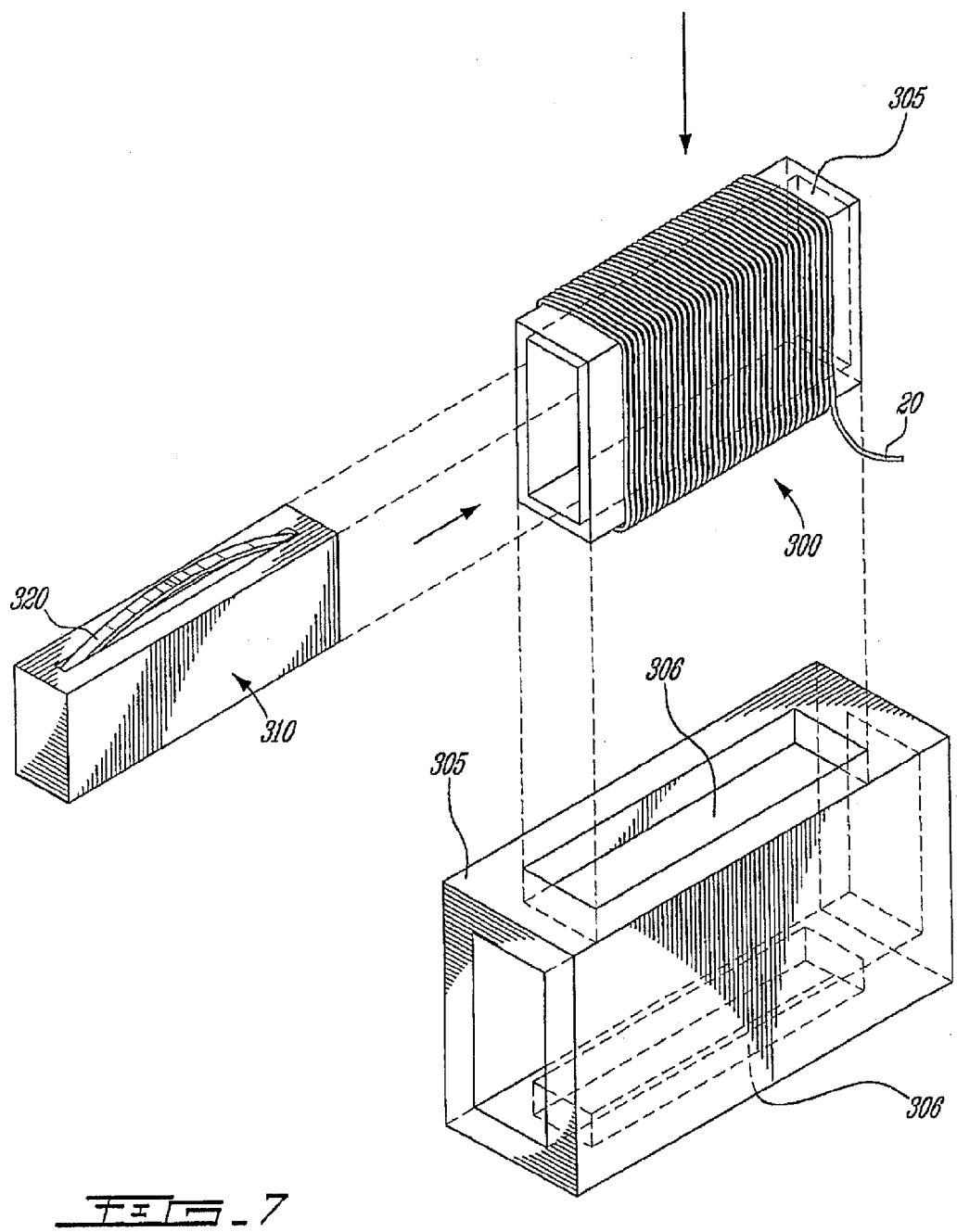
FIG_7

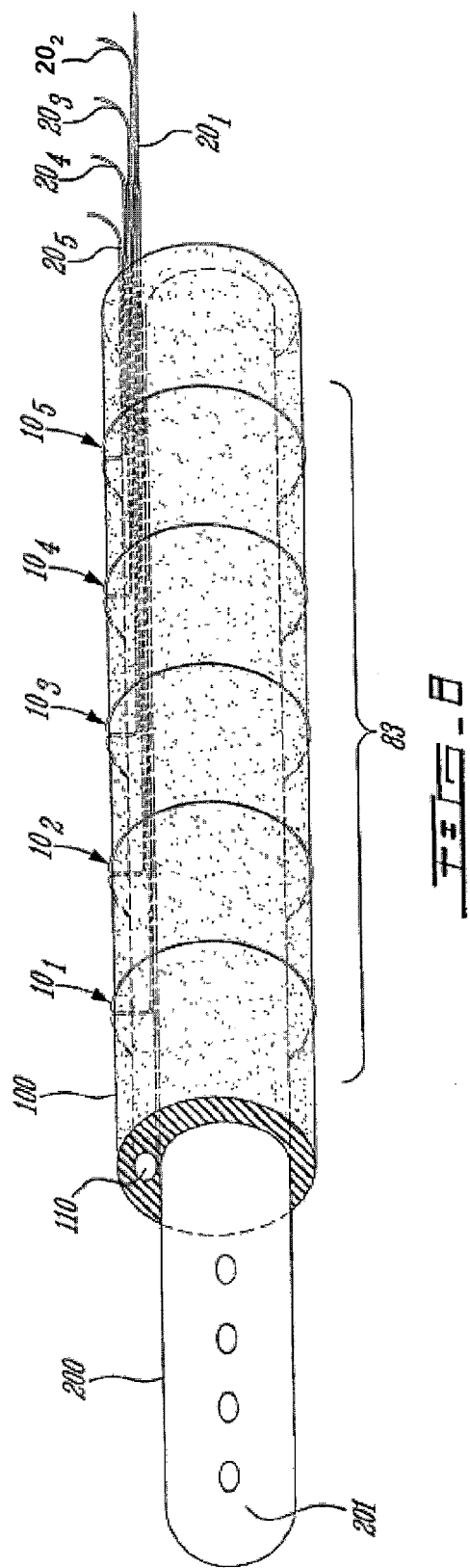

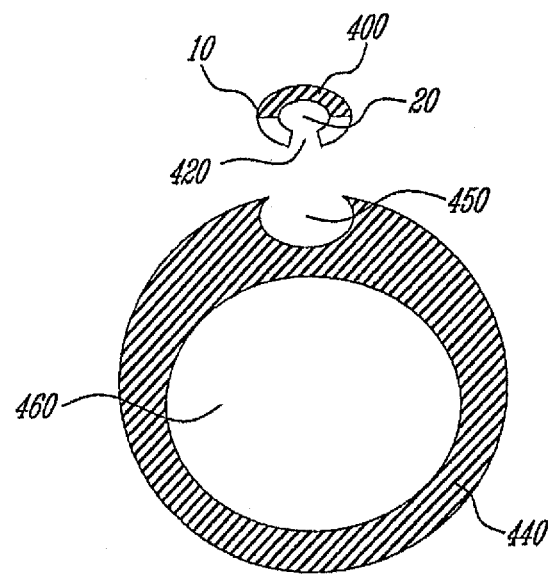
FIG_9
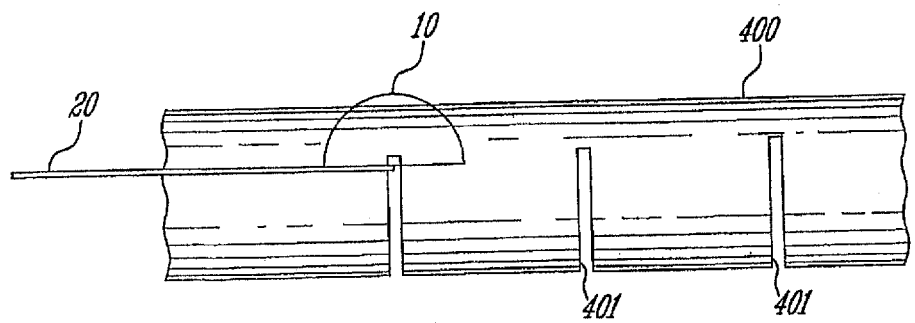
FIG_10

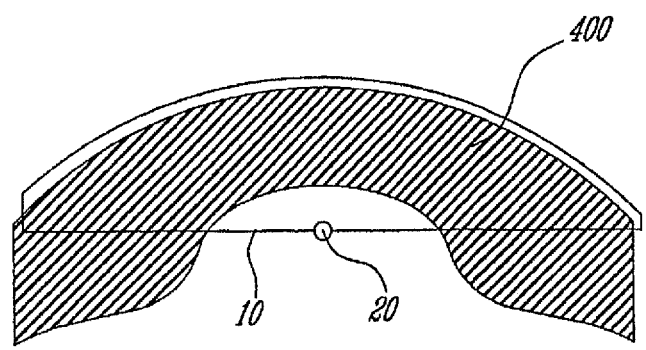
FIG_11A
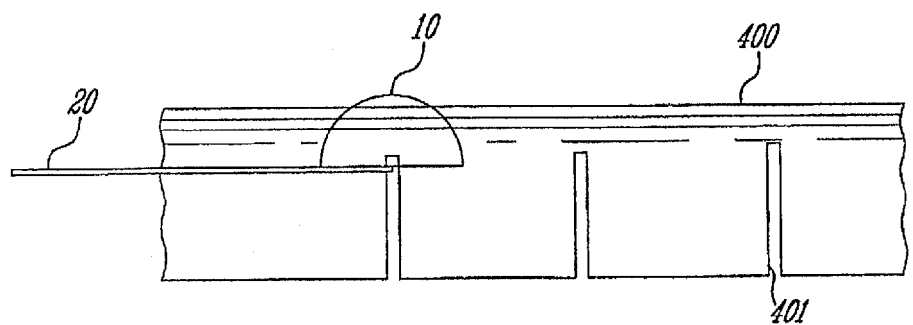
FIG_11B

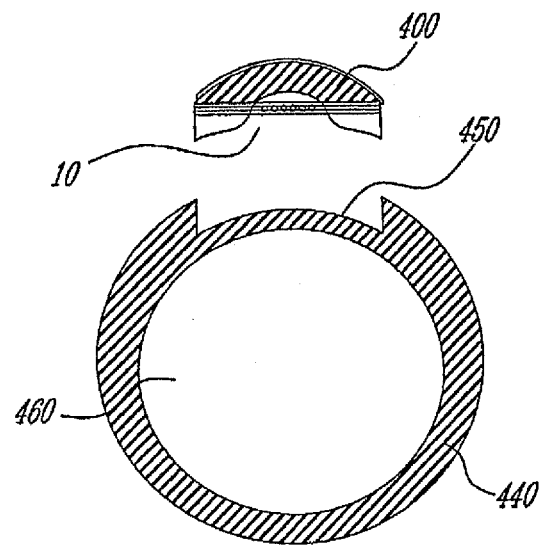
FIG_12
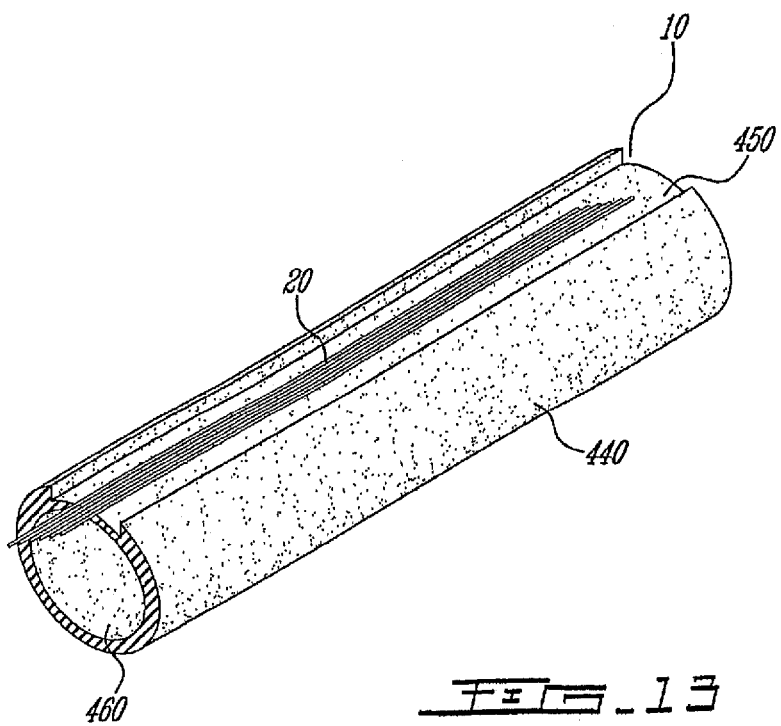
FIG_13

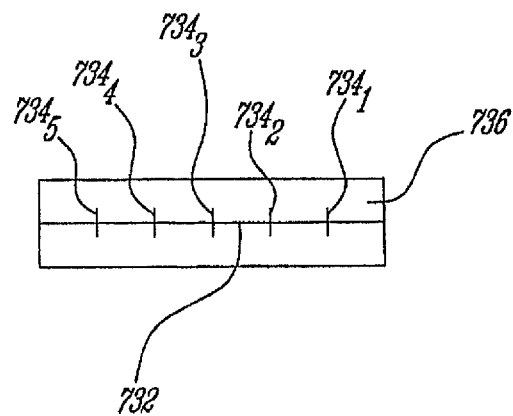
FIG_15
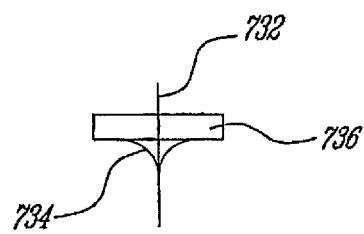
FIG_16

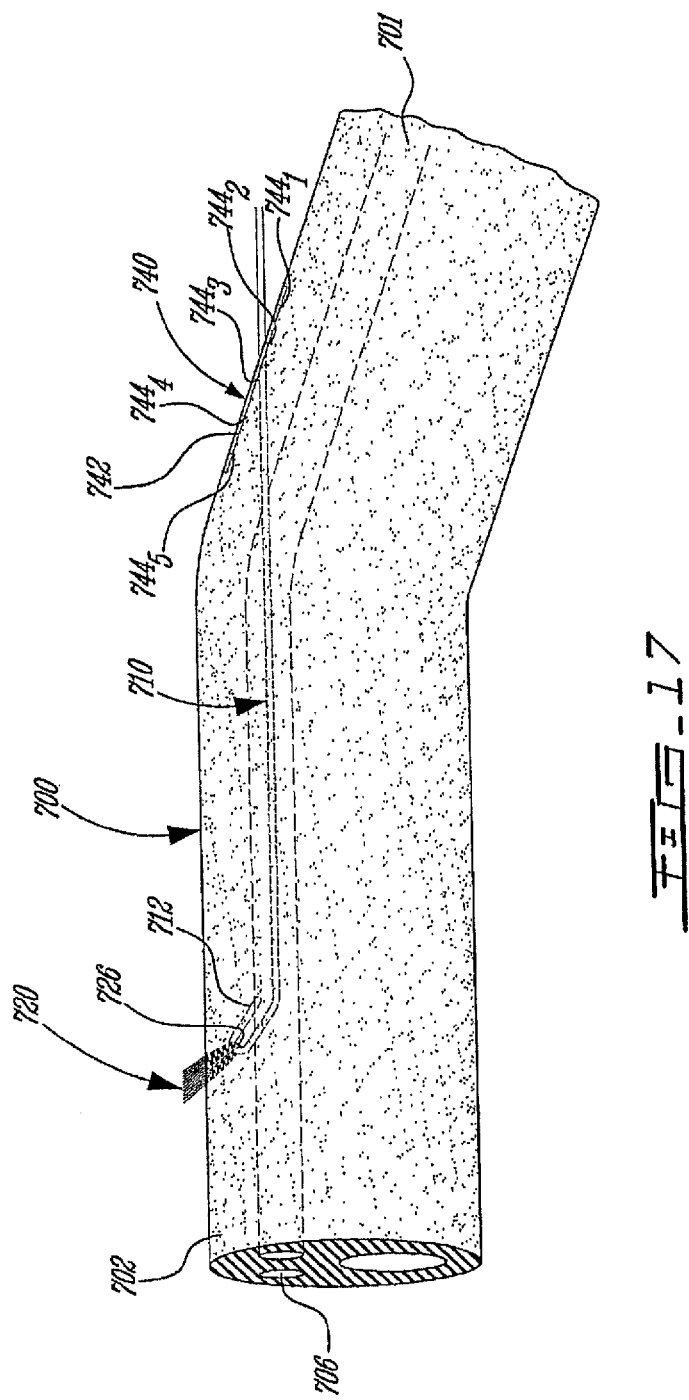

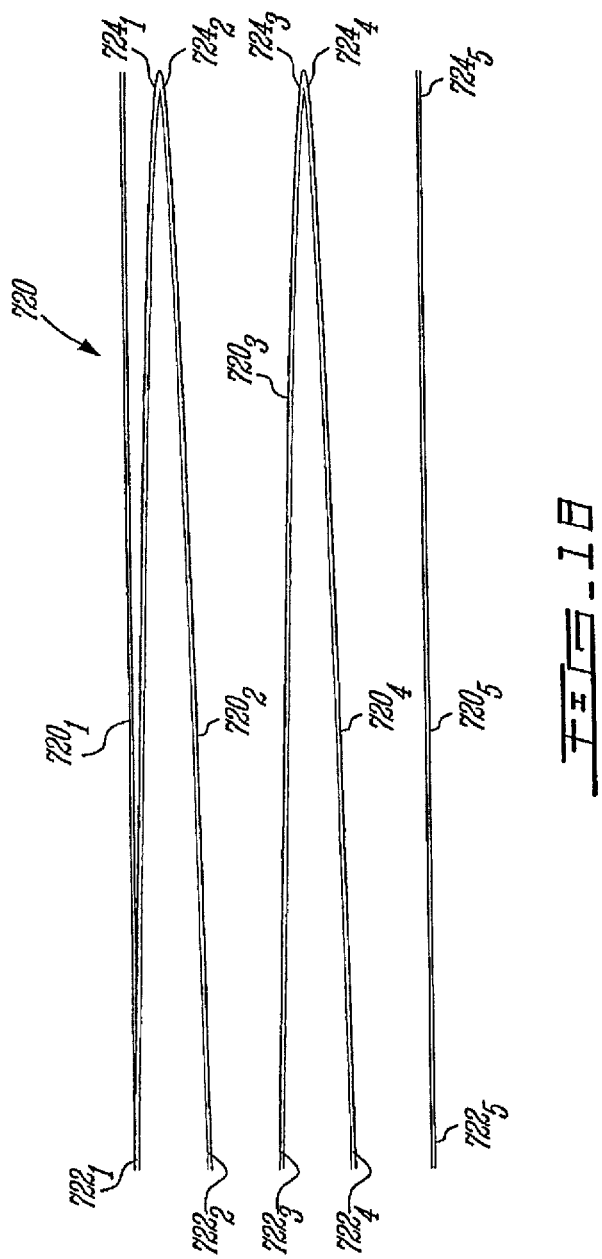

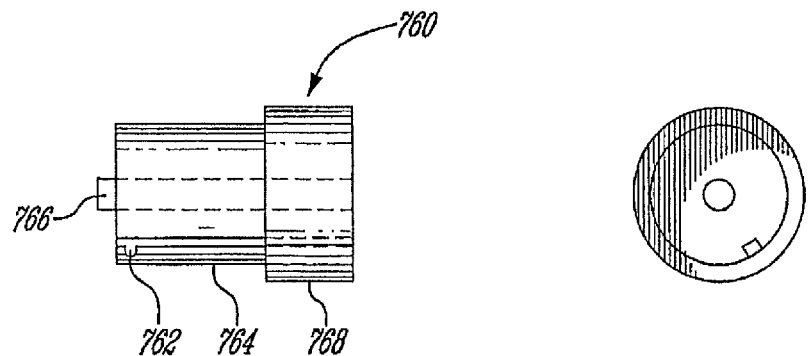
FIG._23A  FIG._23B
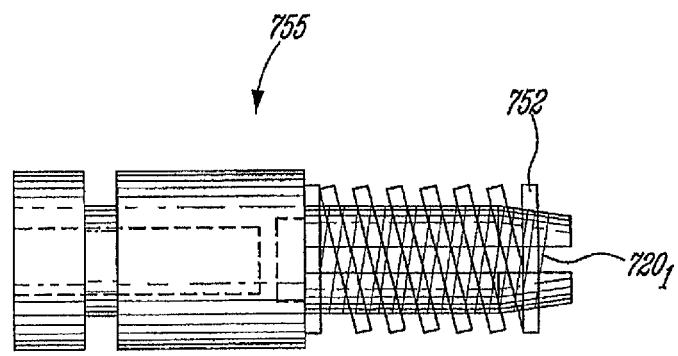
FIG._24

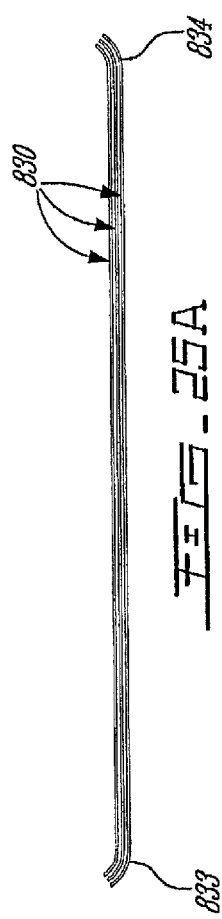
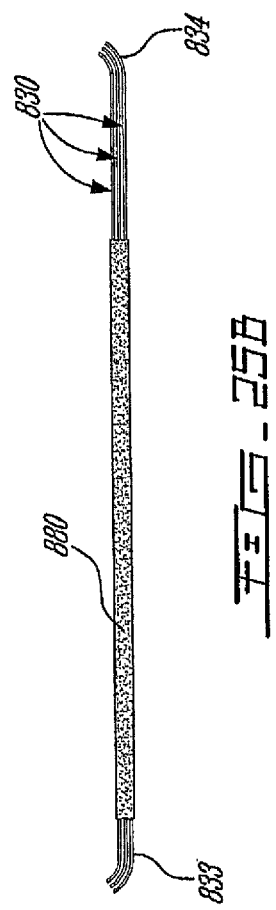
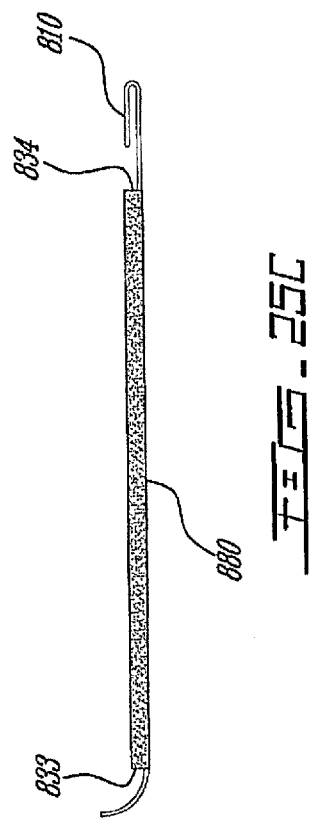

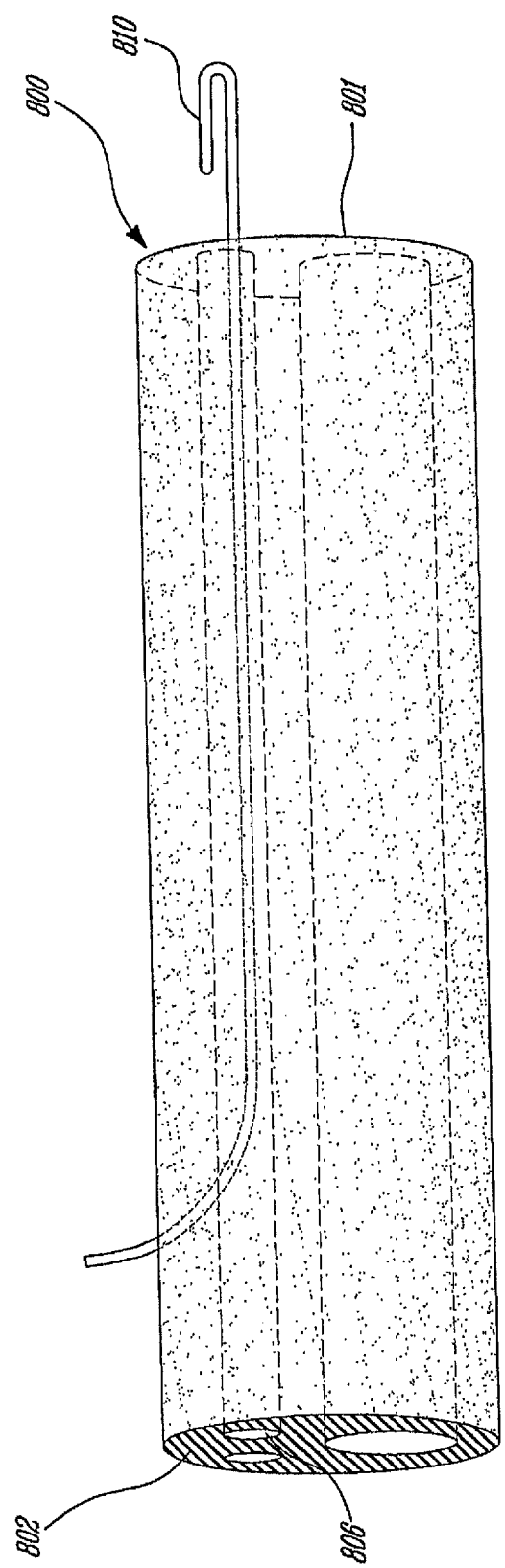

○ plastic fiber or silk
◉ carbon fiber
● cotton core
⦸ stainless steel with insulation ○ plastic fiber or silk
◉ carbon fiber
⦸ stainless steel with insulation

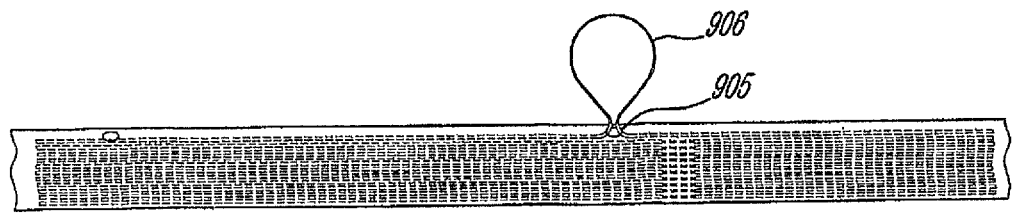
FIG_32
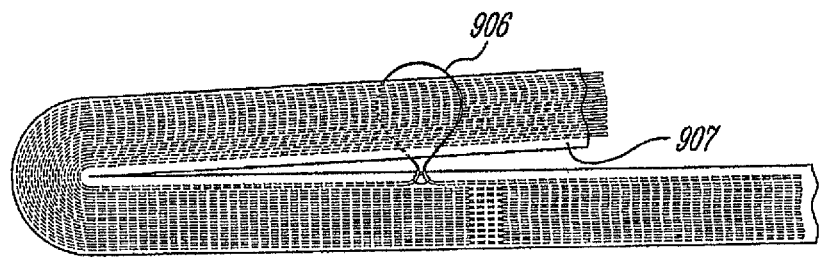
FIG_33
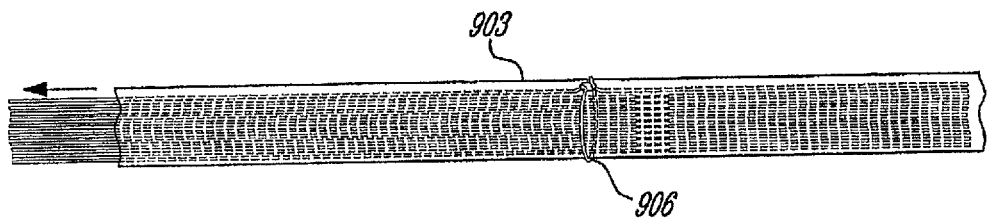
FIG_34

ELECTRODE FOR PHYSIOLOGICAL SIGNAL MEASUREMENTS AND METHOD FOR MAKING SAME

PRIORITY CLAIM

This application is a Continuation of U.S. patent application Ser. No. 11/813,559, now U.S. Pat. No. 8,204,570 filed on Sep. 24, 2007; which is a 371 of PCT Patent Application Serial No. PCT/CA2006/000049 filed on Jan. 12, 2006; which claims priority to U.S. Provisional Patent Appln. Ser. No. 60/643,104 filed on Jan. 12, 2005 and U.S. Provisional Patent Appln. Ser. No. 60/697,381 filed on Jul. 8, 2005.

FIELD OF THE INVENTION

The present invention relates to an electrode that can be mounted to a catheter, and a catheter including at least one such electrode. The invention further includes a method of making the electrode. An assembly of electrodes in accordance with the present invention is suitable for, amongst other things, detection of myoelectrical activity in a patient's muscle, such as the diaphragm or other inspiratory-related muscle.

BACKGROUND OF THE INVENTION

Triggering of ventilatory support systems is usually dependent upon respiratory effort of a patient. Respiratory effort can be detected by measuring myoelectrical activity in a respiratory-related muscle of the patient. A method of measuring such myoelectrical activity is to insert an electrode catheter into the patient's respiratory tract or oesophagus, this electrode catheter being connected to a signal amplifier.

Current manufacturing of electrode catheters typically involves mounting stiff and large contacts that usually come under the form of rings. Those electrodes are commonly mounted directly on the outer surface of the catheter. A large contact area is preferred in catheters of which the electrodes are used for electrical stimulation. In contrast, however, the measurement of myoelectrical signals, e.g. respiratory-related muscle activity via electrodes located in the respiratory tract, does not require such large surface areas.

Although the use of a ring-shaped electrode is advantageous since this structure secures the electrode around the body of the catheter, it has limitations. Typically, ring electrodes are made from sections of rigid or stiff metal tubing as disclosed for example in U.S. Pat. No. 6,588,423 granted to Christer Sinderby on Jul. 8, 2003. This means that upon insertion of a ring electrode catheter, for example a size-16 French nasogastric tube typically of large size relative to the width of the passages in which it is inserted (nostrils, throat, oesophagus, etc.), the ring electrodes can damage the mucosa of the nostrils and/or the upper airways of the patient during both insertion and pulling back of the catheter. In addition to tissue damage, this type of ring electrode catheters can also cause discomfort to the patient. Therefore, there exists a need in the industry to replace rigid metal ring electrodes and to develop narrower and/or smoother electrode catheters that minimise or eliminate tissue damage caused by both insertion and pulling back of an electrode catheter.

Furthermore, the amount of time and effort involved in manufacturing catheters is critical to the price of these catheters. Easy and efficient installation of electrode arrays on a catheter would therefore be of great value.

Last but not least, metals that are approved for the manufacture of electrodes used in a human body are limited. Many of these implant metals are expensive while others are difficult to handle. For example, several types of stainless steel are sanctioned for implantation and can thus be used to make electrodes. However, a great difficulty with stainless steel is that it is very difficult to combine and/or connect with other metals/materials. Accordingly, attachment of stainless steel wires to a connector is not only costly but can also result in a high level of failed connections.

SUMMARY OF THE INVENTION

The present invention proposes an electrode made of a thin metallic thread or wire that overcomes the above discussed drawbacks of the former electrodes. Such electrodes can be mounted on a catheter to detect myoelectrical activity in a patients muscle such as, for example, the diaphragm or other inspiratory-related muscle.

The present invention also proposes a method for making electrodes out of such a thin wire.

More specifically, the present invention concerns a thin-wire, ring-type electrode comprising a loop portion and a wire portion. This electrode is typically made from platinum, gold, titanium, silver, silver chloride or stainless steel, and has a thickness of about $10^{-6}$ m to $10^{-4}$ m. In one embodiment, the electrode comprises a protective coating on the thin wire. Such an electrode is suitable for use with a host tube such as catheter (i.e., an electromyographic (EMG) catheter) or a nasogastric tube.

The present invention further includes a method of making a thin-wire, ring-type electrode as described above, as well a host tube comprising such an electrode, including a catheter or a nasogastric tube, In one embodiment, the method of making the electrode comprises:

winding one end of a thin metal wire around a cylinder to form the loop portion; and fusing the free end of the loop portion of the thin metal wire to the wire portion.

A number of electrodes may be made in accordance with the invention to produce an electrode assembly that is suitable for a host tube, such as a catheter. In one embodiment, the method of making such a catheter comprises:

winding one end of a thin metal wire around a cylinder to form the loop portion of the electrode;

fusing the free end of the loop portion of the thin metal wire to the wire portion;

mounting the loop portion onto the catheter; and inserting the wire portion into the lumen of the catheter.

The electrode catheter itself is comprised of:

an elongated tubular body made of resilient material and having at least one lumen; and an electrode assembly consisting of at least one thin-wire, ring-type electrode having a loop portion and a wire portion, wherein the loop portion is positioned around the tubular body and said wire portion is positioned within the lumen of the tubular body.

In an alternative embodiment to the present invention, a wire carrier may be used to produce an electrode assembly suitable for positioning on a host tube. This wire carrier comprises:

at least one transversal indent through which the loop portion can be mounted on the wire carrier; and a longitudinal, inner groove in which the wire portion of the electrode can be placed.

Yet another alternative method for making a catheter with a thin-wire, ring-type electrode having a loop portion and a wire portion in accordance with the present invention comprises:

inserting a thin-wire electrode bundle that is bent into a U-shape through an opening in the catheter using a guide wire having a hook for engaging the loop part of the U-shaped bundle.

The above and other objects, advantages and features of the present invention will become more apparent upon reading of the following non restrictive description of illustrative embodiments thereof, given by way of example only with reference to the accompanying drawings.

BRIEF DESCRIPTION OF THE DRAWINGS

In the appended drawings:

FIG. 2 is a side view of the cylinder of FIG. 1 with several thin-wire ring-type electrodes in a solution to remove the coating from the ring portion of the thin wire;

FIG. 3 is a side view showing a catheter tubing being inserted into the cylinder of FIGS. 1 and 2 provided with several thin-wire ring-type electrodes;

FIG. 4 is a side view of a catheter tubing being removed from the cylinder thereby transferring the thin-wire ring-type electrodes onto the catheter tubing;

FIG. 5 is a side view of a needle inside the wire lumen of a catheter tubing and piercing the wall of the catheter tubing to hook the thin wire forming a ring-type electrode;

FIG. 7 is a perspective view of elements that make up a connection between a thin-wire ring-type electrode and an amplifier: a hollow box forming a female connector and a male connector;

FIG. 8 is a side view of a nasogastric tube inserted into a catheter tubing with pre-mounted electrodes;

FIG. 9 is a cross-sectional view of a wire carrier and a host tube;

FIG. 10 is a side view of the indented wire carrier of FIG. 9 with a wire loop;

FIG. 11a is a cross-sectional view of an indented wire carrier with a wire loop;

FIG. 11b is a side view of the indented wire carrier of FIG. 11a with a wire loop;

FIG. 12 is a cross-sectional view of an indented wire carrier bearing a series of wire loops, and a host tube; and FIG. 13 is a cross-sectional perspective view of a host tube with a wire carrier bearing a series of wire loops.

FIG. 15 is a cross-sectional view taken along line of the cutting tool of FIG. 14;

FIG. 16 is a cross-sectional view taken along line III-III of the cutting tool of FIG. 14;

FIG. 17 is a partial cross-sectional view of the catheter tubing wherein a bundle of thin-wire electrodes attached to the wire guide hook is being pulled into the catheter tubing as the wire guide distal end is being pulled out of the catheter tubing through a cut in the wall of the catheter tubing;

FIG. 18 is a side view of a bundle of thin-wire electrodes;

FIG. 23 is a combination side (FIG. 23a) and front (FIG. 23b) views of a wrapping tool;

FIG. 24 is a side view of a slitted female contact pin onto which a thin-wire electrode has been mounted;

FIG. 25 shows electrical wires (FIG. 25a) pulled through a prefabricated tube (FIG. 25b) using a wire guide (FIG. 25c);

FIG. 32 is a side elevational view showing a small puncture in the tube of FIG. 31 to fish out a single wire and expose the window strip of this wire to form a small loop;

FIG. 33 is a side elevational view of the tube of FIG. 32 bent to pass through the loop formed by the wire in turn placing the wire around the tubing; and FIG. 34 shows the loop tightened snugly around the tube insuring that the window stripped portion of the wire is fully exposed on the outside of the tube.

DETAILED DESCRIPTION OF THE ILLUSTRATIVE EMBODIMENTS

The non-restrictive illustrative embodiments of the present invention are concerned with an electrode and electrode catheter using thin metallic threads or wires, for example, microwires having diameters as low as $10^{-6}$ to $10^{-4}$ meters or less (there is no known lower limit except with regards to tensile strength of the wire). The embodiments allow for the efficient mounting of at least one electrode on a catheter, resulting in the creation of a flexible ring-microelectrode that is suitable for, amongst other things, the detection of myo-electrical activity in a patient's muscle, such as the diaphragm or other inspiratory-related muscle. Advantageously, and in contrast to older techniques, the method of the present invention does not involve a lot of time consuming wire-by-wire pulling.

EXAMPLE 1

Figure 1:
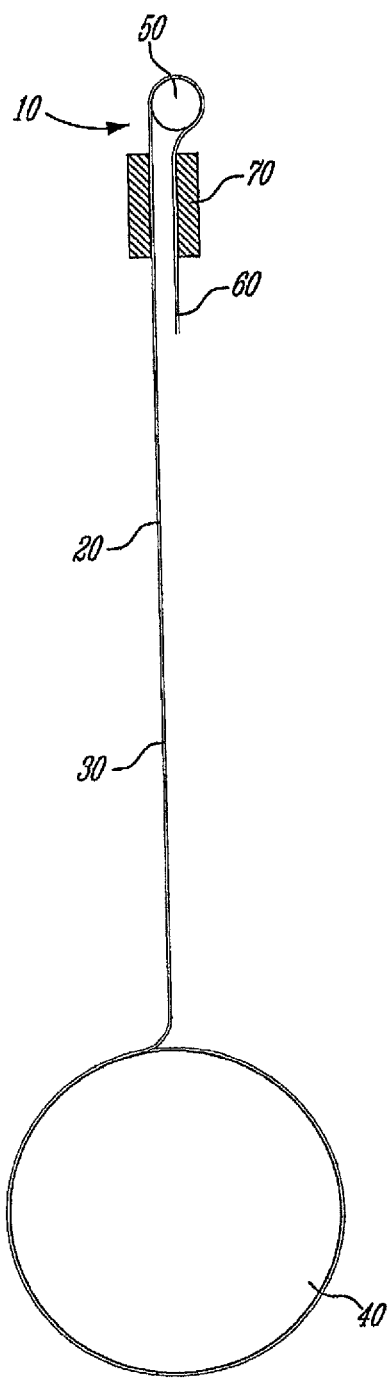
FIG. 1 is a cross-sectional view of a cylinder and clamp device used to fuse into a loop the end of a thin wire from a spool of this wire.

According to a first non-restrictive illustrative embodiment, a thin-wire ring-type electrode for use with a catheter consists of a loop portion 10 and a wire portion 20. A method for making the loop portion 10 and wire portion 20 is illustrated in FIG. 1. A thin wire 30 of suitable metal or alloy from a spool 40 is wound around a hollow cylinder 50 to form a loop 10. The free end 60 of the thin wire 30 is clamped by a clamp device 70 to the wire section 20 for fusion. If a coated thin wire is used, both the free end 60 and the wire portion 20 can be heated by the clamp device 70, thereby heating and fusing the coating. An alternate method when using a coated or non-coated thin wire is to apply an extra layer of coating and then letting the coating dry, with or without heat, to fuse the free end 60 to the wire portion 20. Alternative methods for producing the loop portion 10 of the thin wire 30 are known and may also be used.

In theory any metal, alloy or conducting material such as conducting polymers could be chosen as electrode material since the wet environment of the oesophagus makes the conducting properties less important. However since the electrodes are exposed to the human body the metals, alloys, etc. that can be used are reduced to those that are-non poisonous to the human body. Such materials include, in particular but not exclusively, platinum, gold, titanium, silver, silver chloride and stainless steel as is known to those of ordinary skill in the art. Although stainless steel will be described as a non-limitative example for the material of the electrode in the present and following examples because it is strong, non-corrosive and cheap, other materials such as those indicated in the foregoing description could also be considered as long as the wires that can be made therewith are sufficiently thin.

Once the free end 60 and the wire portion 20 of the thin wire 30 have been fused together, i.e., once the loop 10 of thin wire has been formed, the wire forming the free end 60 is cut close to the fused area and sealed. The wire portion 20 is then cut at a desired length.

The process is repeated along the cylinder 50 at desired interspaces and as many times as required to produce a required number of ring-type electrodes.

Referring now to FIG. 2, the eventual insulation or coating of the loop portions 10 of thin wire is then removed. A method of removing the coating consists of dipping the cylinder 50 along with the array 80 of loop portions 10 in an acid bath or other solvent 90 to dissolve the insulation or coating of the loop portions 10, thereby leaving the wire portions 20 insulated or coated. In an alternative embodiment, a non-coated thin wire is used to make the loop portions 10 and the wire portions 20, and the wire portions 20 are subsequently coated with electrical insulation using techniques known to those of ordinary skill in the art.

Referring now to FIG. 3, the loop portions 10 on the hollow cylinder 50 are then mounted onto a catheter tubing 100 and preferably on a catheter tubing having a wire lumen 110. The catheter tubing 100 is slid into the cylinder 50 provided with the thin wire loop portions 10, as shown in FIG. 3. To facilitate sliding of the catheter tubing 100 into the cylinder 50 with the thin wire loop portions 10, the catheter tubing 100 can be stretched thereby narrowing its diameter. This can be done by first introducing a guide (not shown) into the cylinder 50 and attaching it to the distal end 102 of the catheter tubing 100 to pull onto this distal end. The loop portions 10 are slid off the hollow cylinder 50 at their respective positions on the catheter tubing 100 as the hollow cylinder 50 is removed from the catheter tubing 100, as shown in FIG. 4. When the array 80 of loop portions 10 is in the desired position on the catheter tubing 100, stretching of the catheter tubing 100 is released, thereby expanding its diameter to tightly fit the loop portions 10 around the catheter tubing 100 and thereby fixing the array 80 of loop portions 10 in their respective positions. To avoid entanglement of the free ends of the wire portions 20, the free ends of the wire portions 20 can be temporarily attached to a suitable support (see for example 500 in FIG. 5) or stored on spools (not shown).

After the operation illustrated in FIG. 4 has been completed, the ring-type electrode array 81 (FIG. 5) is in place on the catheter tubing 100, but the wire portions 20 must still be inserted or passed through the wire lumen 110 of the catheter tubing 100. A method for performing this operation is illustrated in FIG. 5.

According to the method of FIG. 5, a needle 120 with an eye 121 near the tip 122 is passed through the wire lumen 110 of the catheter tubing 100 from a proximal end 101 toward the distal end 102 thereof, through the loop portions 10 until the tip 122 of the needle 120 reaches the most distal loop portion $10_1$. Starting from this most distal loop portion $10_1$, the needle tip 122 is pushed to pierce the wall of the catheter tubing 100 until at least a portion (for example, one-half) of the eye of the needle 121 appears on the outside of the catheter tubing 100, preferably near or at the junction between the loop portion $10_1$ and the wire portion $20_1$ of the most distal thin-wire ring-type electrode. To facilitate piercing of the wall of the catheter tubing 100 with the needle tip 122, transversal cuts or holes may be made through the catheter tubing 100 into the wire lumen 110 prior to this process. The free end of the wire portion $20_1$ is then inserted through the eye of the needle 121 and a section of the wire portion $20_1$ is pulled through the eye of the needle 121. The needle 120 is then pulled back away from the distal end 102, thereby inserting the wire portion $20_1$ of the most distal thin-wire ring-type electrode $10_1$, 20 into wire lumen 110 of the catheter tubing 100.

Then, the needle 120 is pulled back until its tip 122 is located close to the second most distal thin-wire loop portion $10_2$ and again the needle tip 122 is pushed to penetrate the wall of the catheter tubing 100 until at least a portion (for example, one-half) of the eye of the needle 121 appears on the outside of the catheter tubing 100, preferably near or at the junction between the loop portion $10_2$ and the wire portion $20_2$ of the second most distal thin-wire ring-type electrode. The free end 130 of the wire portion $20_2$ is passed though the eye of the needle 121 and the wire portion $20_2$ is pulled through the eye of the needle 121. The needle 120 is then pulled back away from the distal end 102 thereby also inserting the wire portion $20_2$ into the wire lumen 110 of the catheter tubing 100 along with the wire portion $20_1$ of the most distal thin-wire ring-type electrode.

Figure 6A:
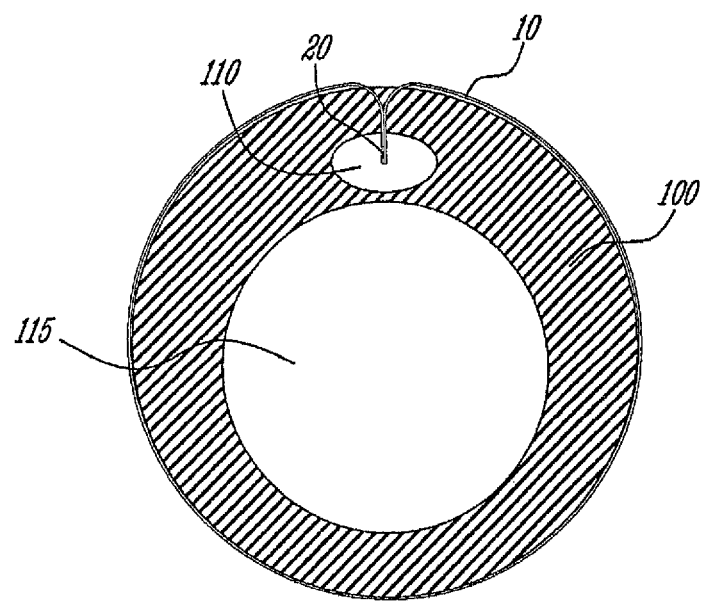
FIG. 6a is a cross-sectional view of a catheter tubing with a wire lumen in which the thin wires forming the ring-type electrodes have been inserted.
Figure 6B:
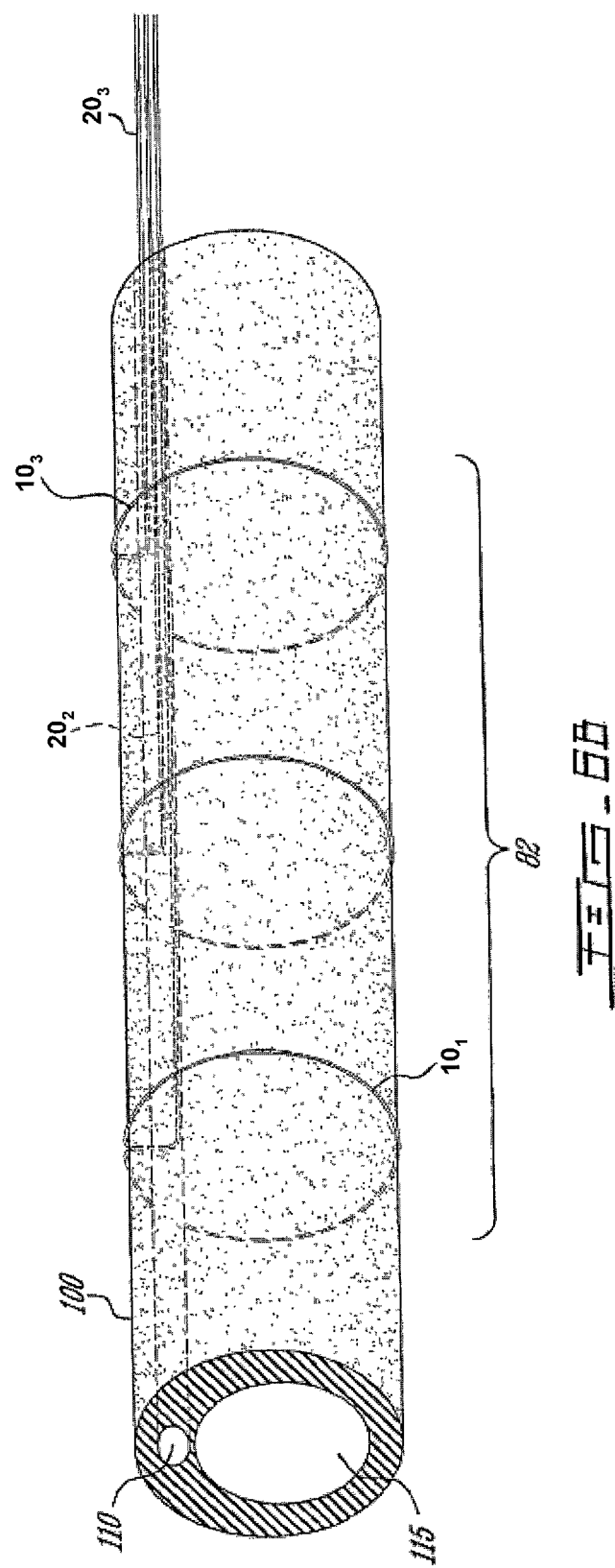
FIG. 6B is a cross-sectional perspective view of a catheter tubing with a wire lumen in which the thin wires forming the ring-type electrodes have been inserted.

The above process is repeated for each thin-wire ring-type electrode $10_3, 20_3$ and $10_4, 20_4$ of the catheter tubing 100 such as to pull by means of the needle 121 all the wire portions 20 within the wire lumen 110 of the catheter tubing 100, as shown in FIGS. 6a and 6b. A method using several needles for simultaneously piercing several point of the wall of the catheter tubing 100 to simultaneously pull a plurality of wire portions 20 may also be envisaged without departing from the present invention. Also, the number of thin-wire ring-type electrodes 10,20 is not restricted to four (4).

Once at least a portion of all the wire portions $20_1, 20_2, 20_3$ and $20_4$ have been pulled into the wire lumen 110 of the catheter tubing 100, the needle 120 is pulled from the wire lumen 110 of the catheter tubing 100 such that at least a portion of each of the wire portions $20_1, 20_2, 20_3$ and $20_4$ protrudes from the proximal end 101 of the wire lumen 110. While the wire portions $20_1, 20_2, 20_3$ and $20_4$ are still inserted in the eye of the needle 120, a shield and/or insulating tubing can be pushed over the end of the needle 120 opposite to the tip 122. The insulating tubing is pushed past the tip of the needle 122, over the wire portions $20_1, 20_2, 20_3$ and $20_4$ until it reaches the proximal end 101 or a position close to the proximal end 101 of the wire lumen 110 of the catheter tubing 100 on which the loop portions $10_1$, $10_2$, $10_3$ and $10_4$ are mounted, such as to cover at least a portion of the wire portions $20_1$, $20_2$, $20_3$ and $20_4$ protruding from the wire lumen 110. The shield and/or insulating tubing is then pushed further into the wire lumen 110 of the catheter tubing 100 and secured to this position such that none of the wire portions $20_1$, $20_2$, $20_3$, $20_4$ are exposed near the proximal end 101 of the wire lumen 110.

Then, the loop portions $10_1$, $10_2$, $10_3$ and $10_4$ on the outside of the catheter tubing are covered and the holes created in the wall of the catheter tubing 100 by the needle 120 are filled. This covering and hole filling is performed by dipping the electrode array 82 on the catheter tubing 100 (see FIG. 6b) in a coating bath or other alternative device (not shown) while ensuring that no dipping material/coating enters the large catheter lumen 115 of the catheter tubing 100 that bears the loop portions $10_1$, $10_2$, $10_3$ and $10_4$.

Referring now to FIG. 8, the electrode array 83 on the catheter tubing 100 is mounted or slid on a nasogastric tube 200. To facilitate the mounting or sliding of the catheter tubing 100, the nasogastric tube 200 can be stretched thereby narrowing its diameter. This can be done by first introducing a guide (not shown) in the large catheter lumen 115 of the catheter tubing 100 and attaching it to the distal end 201 of the nasogastric tube 200 to pull onto the distal end 201. When the electrode array 83 is in the desired position, stretching of the nasogastric tube 200 is released, thereby expanding its diameter and fixing the electrode array 83 in this position. For example, to ensure that the electrode array 83 is fixedly secured in position on the nasogastric tube 200, this nasogastric tube 200 can be coated with glue or similar compound or treated with a solvent prior to the release of the stretch. Other fastening or securing methods known to those of ordinary skill in the art may also be used.

The above described method for mounting an electrode array 83 can be either applied to a separate catheter tubing 100 which is then mounted on a nasogastric tube 200 as shown in FIG. 8, or directly on a nasogastric tube whereby the operation illustrated in FIG. 8 is no longer required.

Use of thin wires, for example microwires having diameters of the order of $10^{-6}$ to $10^{-4}$ meters, to form a ring around a catheter can efficiently serve as an electrode to measure signals when surrounded by bodily fluids or electrolyte charged materials. Also, when fully annealed and curved, the ring-like thin-wire electrodes are soft and flexible, allowing them to flex or bend with the catheter without damaging surrounding tissue. Moreover, by using thin wires it is possible to coat the exterior of the array such that none of the metallic electrodes actually comes into contact with bodily tissues or fluids, thereby permitting the use of a wider variety of metals or alloys to manufacture the electrodes.

The resulting array of thin-wire ring-type electrodes can be dipped into a solution to control resistivity between the different pairs of laterally adjacent electrodes, as taught by International patent application No. PCT/CA2004/000550 filed on Apr. 8, 2004. In the same manner, the resulting array of thin-wire ring-type electrodes can be used in combination with a motion-artifact-reducing interface applied to the electrodes to prevent direct contact between tissues of the living body and the electrodes, as taught by International patent application PCT/CA99/00652 filed on Jul. 16, 1999. This applies to all of various embodiments described below.

In a non-restrictive illustrative embodiment, the hollow cylinder 50 shown in FIGS. 1 and 2 can be replaced by a grooved and indented wire carrier 400, of which examples are illustrated in FIGS. 9, 10, 11a and 11b. The wire carrier 400 can be of any desired shape and size, examples of which are shown in FIGS. 9, 10, 11a and 11b. Wire carrier 400 is formed with a series of transversal indents such as 401 at desired intervals through which the loop portions 10 can be mounted onto the wire carrier 400 by using, for example, the method shown in FIGS. 1, 2 and 3 or any other method of fixing the wire loops onto the wire carrier 400. The wire carrier 400 also has a longitudinal, inner groove 420 in which the wire portions 20 can be placed as shown in FIGS. 10, 11 and 12, thereby not necessitating the insertion of the insulated wire portions 20 as illustrated in FIGS. 5, 6a and 6b.

After the bared wire loop portions 10 have been mounted on the wire carrier 400 and after the insulated wire portions 20 have been placed inside the wire carrier 400, the wire carrier 400 can be mounted onto a host tube 440 (for example a nasogastric tube) with a lumen 460 and a groove 450 adapted to receive the wire carrier 400, as shown, for example, in FIGS. 9 and 12. The wire carrier 400 is secured in the groove 450 using mechanical means such as clipping, glue or any other method known to those of ordinary skill in the art.

A complete array according to the non-restrictive illustrative embodiment of FIGS. 9-12 is shown in FIG. 13.

In operation, the thin-wire ring-type electrode array according to the illustrative embodiments of the present invention must be connected to a proper amplifier device. Referring now to FIG. 7, a method of connecting an electrode catheter to an amplifier is shown. Instead of soldering a wire to a connector, which can be problematic when using stainless steel, for example, and to avoid poor connections due to an intermediate connector, the proposed method consists of using the wire portions 20 as contact areas for the electrode array. This method requires no solder equipment. To construct a female connector 300, the insulation is first removed from each wire portion 20. Each wire portion such as 20 is wound around a hollow box 305 made of conductive or non-conductive material with openings from the inside out of the hollow box 305, for example, windows 306 to permit direct contact with the wire portion 20 from the inside of the hollow box 305. The wound wire portion 20 is secured on the hollow box 305 by encapsulating it with glue, plastic or other adequate coating (not shown). The operation is repeated individually for each of the other wire portions 20, each wire being wound around a separate box 305. Each box is then mounted into a main connector body (not shown). The male connector 310 simply comprises spring loaded wires that, when inserted into the female connector 300, will contact the wound wire portion 20 of the female connector from the inside of the hollow box 305 through the windows 306. The male connector 310 is connected directly to an amplifier through a wire such as 320.

Alternatively, the wire portion 20 itself can be used as a connector. For example, the wire portion 20 can be wound onto a spool or otherwise shaped to form a connector receptacle capable of receiving a male spring-loaded connector plug. In the same manner, the wire portion 20 can be wound on a spool or otherwise shaped to form a connector plug capable of being received into a spring-loaded connector receptacle.

EXAMPLE 2

The following describes an alternative method of making an electrode in accordance with the present invention.

Figure 14:
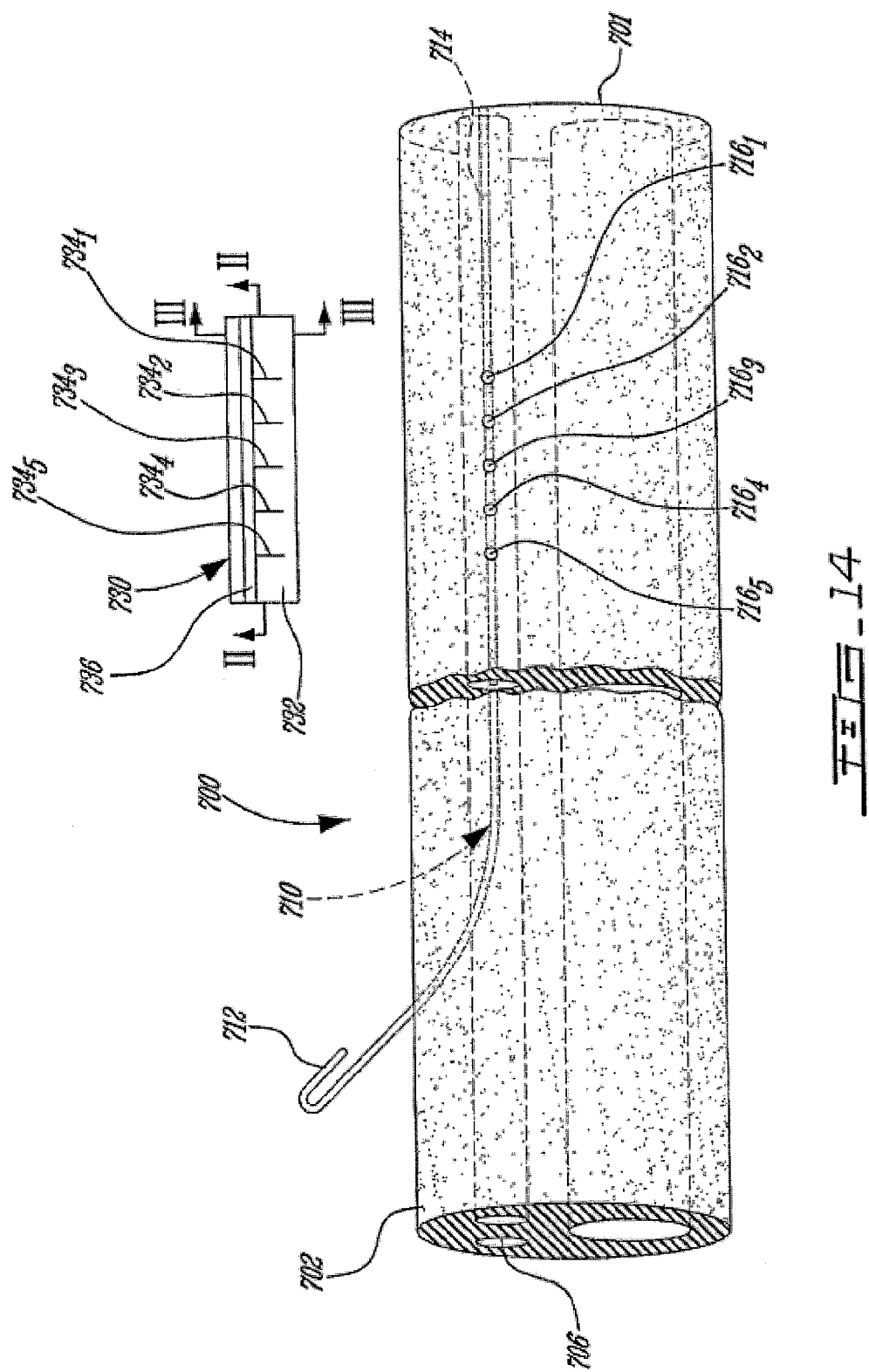
FIG. 14 is a partial cross-sectional view of a catheter tubing, having a guide wire inserted therein, and an associated cutting tool.

Turning now to FIG. 14 of the appended drawings, a catheter tubing 700 provided with three lumens (only one of which is identified, namely lumen 706). FIG. 14 also shows tools used in the placement of electrodes onto the catheter tubing 700, namely a guide wire 710, which is inserted into one of the lumens 706, as well as a cutting tool 730 placed adjacent the distal end 701 of the catheter tubing 700. The catheter tubing 700 is advantageously made of resilient material, for example plastic material.

According to the non-restrictive illustrative embodiment shown in FIG. 14, the guide wire 710 having a hook 712 at its proximal end is inserted into the lumens 706 at the proximal end 702 of the catheter tubing 700. As better illustrated in FIGS. 15 and 16, the cutting tool 730, which is used to make a controlled opening 740 (see FIG. 17) into the wall of the catheter tubing 700 near its distal end 701, comprises a razor-blade 732 with elevated perpendicular knifes $734_1$, $734_2$, $734_3$ $734_4$, $734_5$ and a stopper 736 at the top of the knives 734.

Referring to FIGS. 16 and 17, when the cutting tool 730 is applied to the catheter tubing 700, the razorblade 732 creates a lengthwise slit 742 while the knives $734_1$, $734_2$, $734_3$, $734_4$, $734_5$ create short rips $744_1$, $744_2$, $744_3$, $744_4$, $744_5$ radial to the catheter tubing 700. The stopper 736 defines the depth of the rips $744_1$, $744_2$, $744_3$, $744_4$, $744_5$ into the wall of the catheter tubing 100. It is to be understood that even though five knives $734_1$, $734_2$, $734_3$, $734_4$, $734_5$ are shown, any number of knives may be used depending on the application. Optionally, as may be better seen from FIG. 14, the distal end 714 of the wire guide 707 may have markings 716 for the positioning of the cutting tool 730 knives $734_1$, $734_2$, $734_3$, $734_4$, $734_5$ onto the wall of the catheter tubing 700.

A thin-wire electrode bundle 720 is bent into a U-shape, the loop part 726 of which is engaged with the hook 712 of the guide wire 710. The thin-wire electrode bundle 720, shown in FIG. 18, is composed of individual thin-wire electrodes $720_1$, $720_2$, $720_3$, $720_4$, $720_5$ which are insulated except for each of their respective ends $722_1$, $722_2$, $722_3$, $722_4$, $722_5$ and $724_1$, $724_2$, $724_3$, $724_4$, $724_5$. After the opening 740 has been created into the wall of the catheter tubing 700 using the cutting tool 730, the guide wire 710 is retracted through the opening 740 so that the distal end 714 of the guide wire 710 starts protruding from the lengthwise slit 742. The catheter tube 700 may then bend so that the guide wire 710 may be pulled through the slit 742, which in turn pulls the loop part 726 of the electrode wire bundle 720 through the slit 742 as well.

Figure 19:
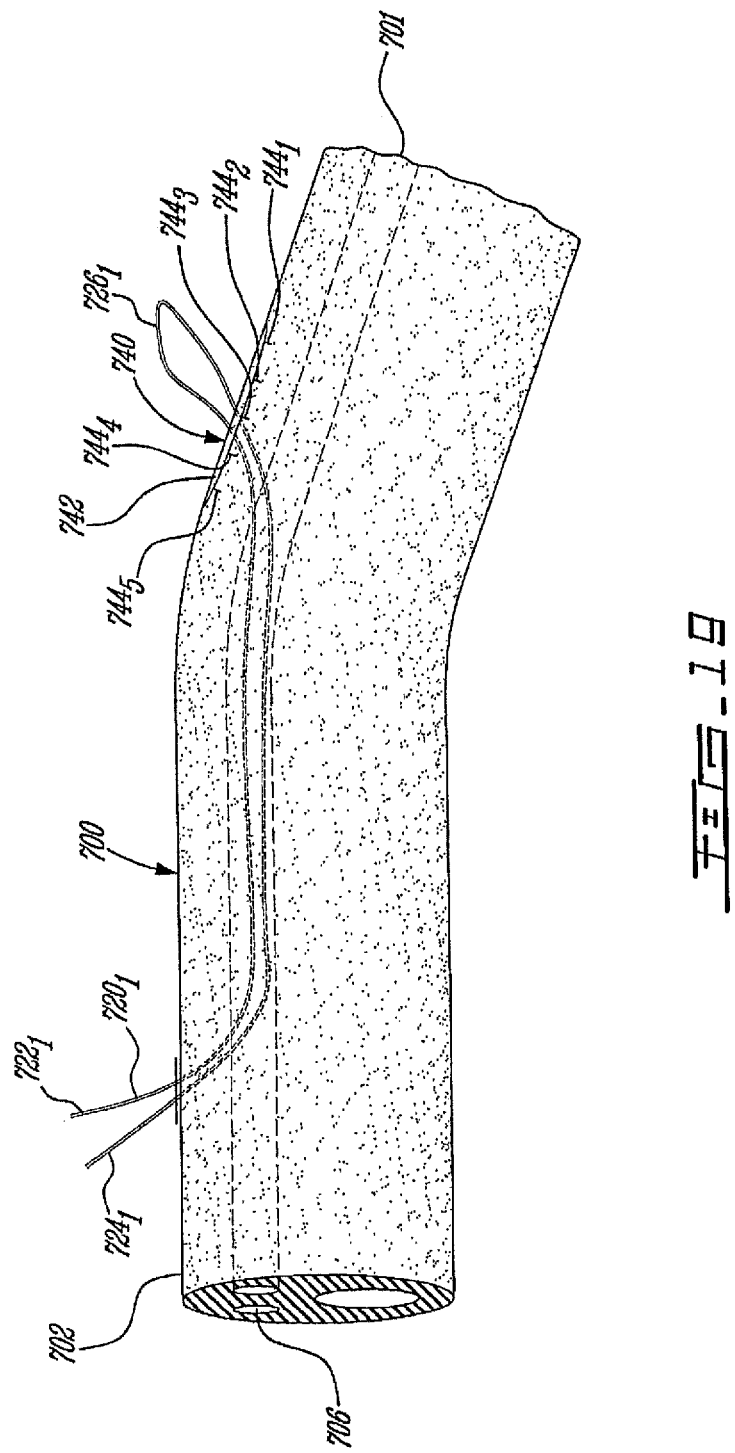
FIG. 19 is a partial cross-sectional view of a thin-wire electrode inside the catheter tubing, the thin-wire electrode having a loop portion exiting the catheter tubing through a cut in the wall of the catheter tubing.

After the wire guide 710 has exited the catheter tubing 700 through the opening 740, the loop part 726 of the thin-wire electrode bundle 720 is disengaged from the hook 712 of the wire guide 710. For the sake of clarity, FIG. 19 illustrates a single thin-wire electrode $720_1$ having a loop part $726_1$ protruding from the opening 740. The loop part $726_1$ is then positioned around the distal end 701 of the catheter tubing 700 and placed in a corresponding rip $44_1$ (see FIG. 20). By pulling the ends $722_1$, $724_1$ corresponding to the loop $726_1$ at the proximal end 702 of the catheter tubing 700, the loop part $726_1$ is tightened around the catheter tubing 700. The radial rip $744_1$ prevents the loop part $726_1$ from being tilted towards the proximal end 702 of the catheter tubing 700. The above process is repeated for each of the remaining thin-wire electrodes $720_2$, $720_3$, $720_4$, $720_5$.

Once the thin-wire electrodes $720_1$, $720_2$, $720_3$, $720_4$, $720_5$ are positioned within their respective rips $744_1$, $744_2$, $744_3$, $744_4$, $744_5$, the opening 740 may be closed by slightly pulling at the respective ends $722_1$, $722_2$, $722_3$, $722_4$, $722_5$ and $724_1$, $724_2$, $724_3$, $724_4$, $724_5$ of the thin-wire electrodes $720_1$, $720_2$, $720_3$, $720_4$, $720_5$. A slight bend of the catheter tubing 700 may help ensure that the thin-wire electrodes $720_1$, $720_2$, $720_3$, $720_4$, $720_5$ are not stuck in the opening 740 as its closes. In order not to interfere with already positioned thin-wire electrodes $720_1$, $720_2$, $720_3$, $720_4$, $720_5$, it may be advantageous to start positioning the thin-wire electrodes $720_1$, $720_2$, $720_3$, $720_4$, $720_5$ most towards the proximal end 702 of the catheter tubing 700. Since all the ends $722_1$, $722_2$, $722_3$, $722_4$, $722_5$ and $724_1$, $724_2$, $724_3$, $724_4$, $724_5$ of each of the thin-wire electrodes $720_1$, $720_2$, $720_3$, $720_4$, $720_5$ are at the proximal end 702 of the catheter tubing 700, the risk of having loose electrode ends sticking out in the distal end 701 is eliminated.

Use of thin-wires, for example, microwires having diameters of the order of $10^{-6}$ to $10^{-4}$ meters, to form loops around a catheter may efficiently serve as electrodes to measure signals when surrounded by bodily fluids or electrolyte charged materials. Also, when fully annealed and curved, the loop thin-wire electrodes are soft and flexible, allowing them to flex or bend with the catheter without damaging surrounding tissue. Moreover, by using thin-wires it is possible to coat the exterior of the array such that none of metallic electrodes actually comes into contact with bodily tissues or fluids, thereby permitting the use of a wider variety of metals or alloys to make the electrodes.

Referring to FIGS. 21, 22, 23 and 24, and with reference back to FIGS. 18, 19 and 20, after the thin-wire electrodes $720_1$, $720_2$, $720_3$, $720_4$, $720_5$ have been positioned around the catheter tubing 700, their respective ends $722_1$, $722_2$, $722_3$, $722_4$, $722_5$ and $724_1$, $724_2$, $724_3$, $724_4$, $724_5$ may be wound around a slitted female or male contact pin 755 using a wrapping tool 760 which also releases a spring 752 over the thin-wire electrodes $720_1$, $720_2$, $720_3$, $720_4$, $720_5$. The wrapping tool 760 may also be used as an insertion tool for mounting the contact pin 755 in a plastic contact housing (not shown). For the sake of clarity, only the female version of the contact pin 755 and one thin-wire electrode $720_1$ are illustrated, though it is to be understood that a male contact pin may be used as well and that the procedure holds for all remaining thin-wire electrodes $720_2$, $720_3$, $720_4$, $720_5$.

The wrapping tool 760 keeps the thin-wire electrodes $720_1$, $720_2$, $720_3$, $720_4$, $720_5$ in place as they are wrapped around the contact pin 755. A notch 762 in the spring support 764 of the wrapping tool 760 acts as a channel for the thin-wire electrodes $720_1$, $720_2$, $720_3$, $720_4$, $720_5$. This means that the thin-wire electrodes $720_1$, $720_2$, $720_3$, $720_4$, $720_5$ are put through the spring support 764 before the spring 752 is pressed onto the contact pin 755. As the contact pin 755 is spun using the rotating pin 766, the spring 752 is pushed away from the spring support 764 by the spring push-out 768 and lands on the thin-wire electrodes $720_1$, $720_2$, $720_3$, $720_4$, $720_5$ that are being spun in the opposite direction. When the spinning is finished, constant pressure between the thin-wire electrodes $720_1$, $720_2$, $720_3$, $720_4$, $720_5$ and the contact pin 55 is provided by the spring 752.

As a final step, the distal end 701 of the catheter tubing 700 may be dipped in a curing solvent such as, for example, D3 that with capillary force fills the lengthwise slit 742 and seals the radial rips $744_1$, $744_2$, $744_3$, $744_4$, $744_5$.

Alternatively, the thin-wire electrode ends $722_1$, $722_2$, $722_3$, $722_4$, $722_5$ and $724_1$, $724_2$, $724_3$, $724_4$, $724_5$ may be used as connectors. For example, the thin-wire electrode ends $722_1$, $722_2$, $722_3$, $722_4$, $722_5$ and $724_1$, $724_2$, $724_3$, $724_4$, $724_5$ may be wound onto a spool or otherwise shaped to form a connector receptacle capable of receiving a male spring-loaded connector plug. In the same manner, the thin-wire electrode ends $722_1$, $722_2$, $722_3$, $722_4$, $722_5$ and $724_1$, $724_2$, $724_3$, $724_4$, $724_5$ may be wound on a spool or otherwise shaped to form a connector plug capable of being received into a spring-loaded connector receptacle. Furthermore, reliable connection to electrical contacts may also be improved by using a redundant wire.

EXAMPLE 3

An alternative to the above described embodiments comprises the following mechanical modification in respect of an electromyographic (EMG) catheter.

One of the problems associated with installing a number of isolated very thin (for example, 60 μm thin) stainless steel wires 830 (FIG. 25a) into a small lumen in the catheter is that it is difficult to keep the wires together, as they tend to get themselves entangled. This problem makes it difficult to adjust the wires so that just the part that is without isolation in on the outside of the catheter.

It has been found practical to collect all wires using a braided tube (not shown) with just a very thin wall which has a low friction to the catheter and to the isolation on the wires. The use of cable braids in electrical assemblies is common, preferably as protective cover keeping multiple cables together. The braid is a woven mesh like tube made of synthetic material, and has the property that the diameter of the tube is reduced if the tube is stretched and vice versa. If the applied stretching of the tube is removed, the tube will expand to its natural diameter as is well known to a person skilled in the art. Braid like tubes of silk are also known from medical applications, sutures, but these are not as resilient/easily expanded as the synthetic braids. A novel method to use a braid as an active part in EMG catheter will be described in detail herein below.

The wires can be braided loosely by machine so that the desired wire length is cut from a spool and the ends are uncovered by removing the braided tube by heat or other suitable means. Preferably the proximal end 833 has a minor part of the braid uncovered compared to the distal end 834 where the electrode loops are to be formed. The wires are then readily isolated. Alternatively, the wires may be pulled through a prefabricated braided tube 880 using a guide wire 810, as illustrated in FIG. 25b and FIG. 25c.

Figure 26A:
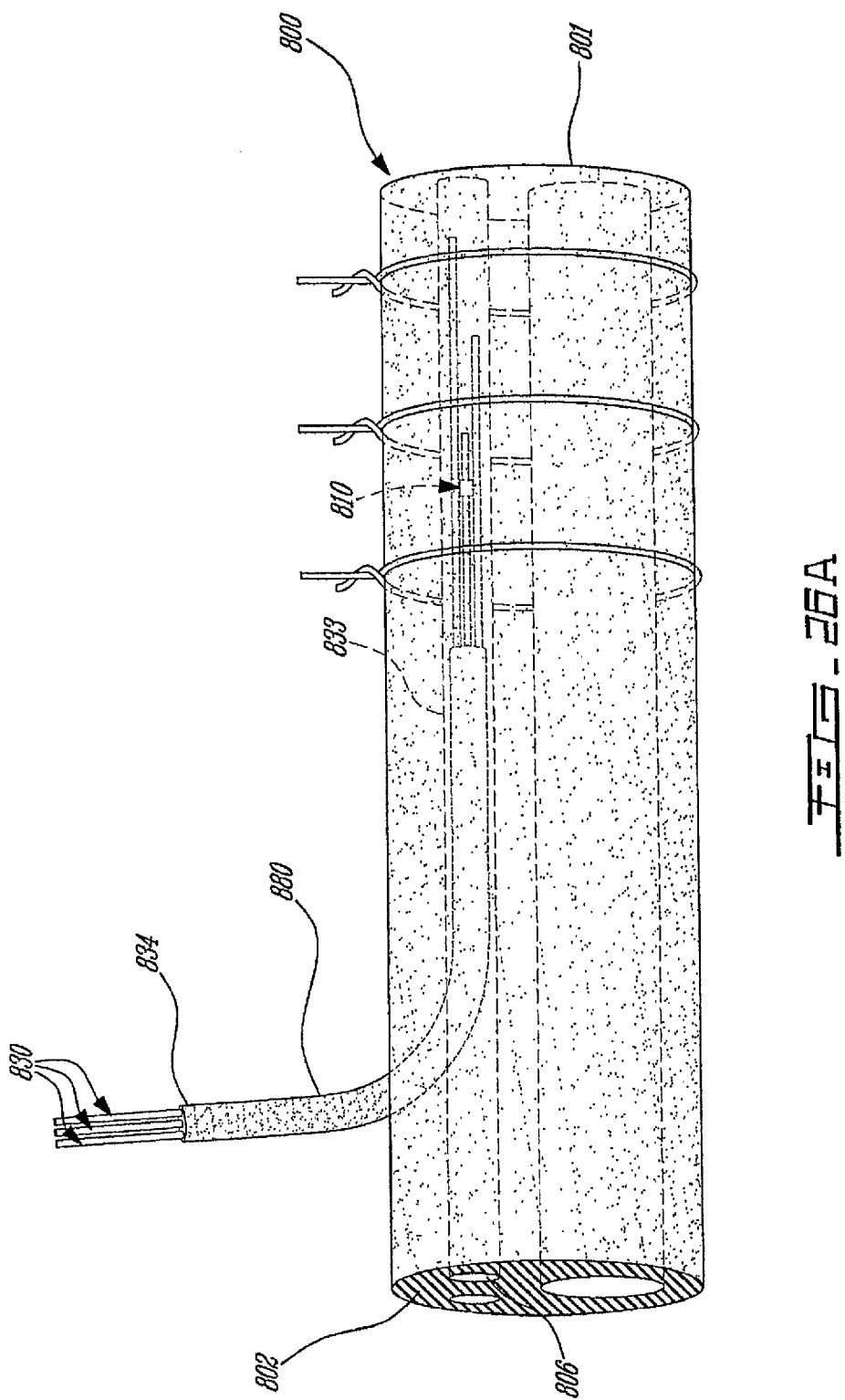
FIG. 26 shows the installation in a catheter of wires grouped in a prefabricated braided tube (FIG. 26a) with the aid of a guide wire (FIG. 26b)

To install the wires in the catheter 800, a guide wire 810 with a hook at its distal end is inserted through a hole in a lumen 806 of the catheter at the proximal end 802 of the catheter as shown schematically in FIG. 26b. When the hook appears in a hole on the distal end 801 of the catheter, the hook is inserted into the proximal end 833 of the braid holding the wire bundle. The braided tube can now be pulled through the lumen 806 to the proximal end 802, and the proximal end 834 of the braid is pulled out of the lumen 806 at the proximal end 802 or through the side of the proximal end 802 of the catheter. Since the braid itself tends to squeeze the wires as the braid is elongated, the wires are held together by the compression force induced by the hook and a force holding the braid at the distal end 834, there will be less risk of the wires getting entangled within the lumen 806 when pulled through the lumen (FIG. 26a).

Loops are made in the vicinity of the distal end 801. At the proximal end 802, the braided hose runs in a plastic tube for protection to a male connector (not shown).

Figure 27A:
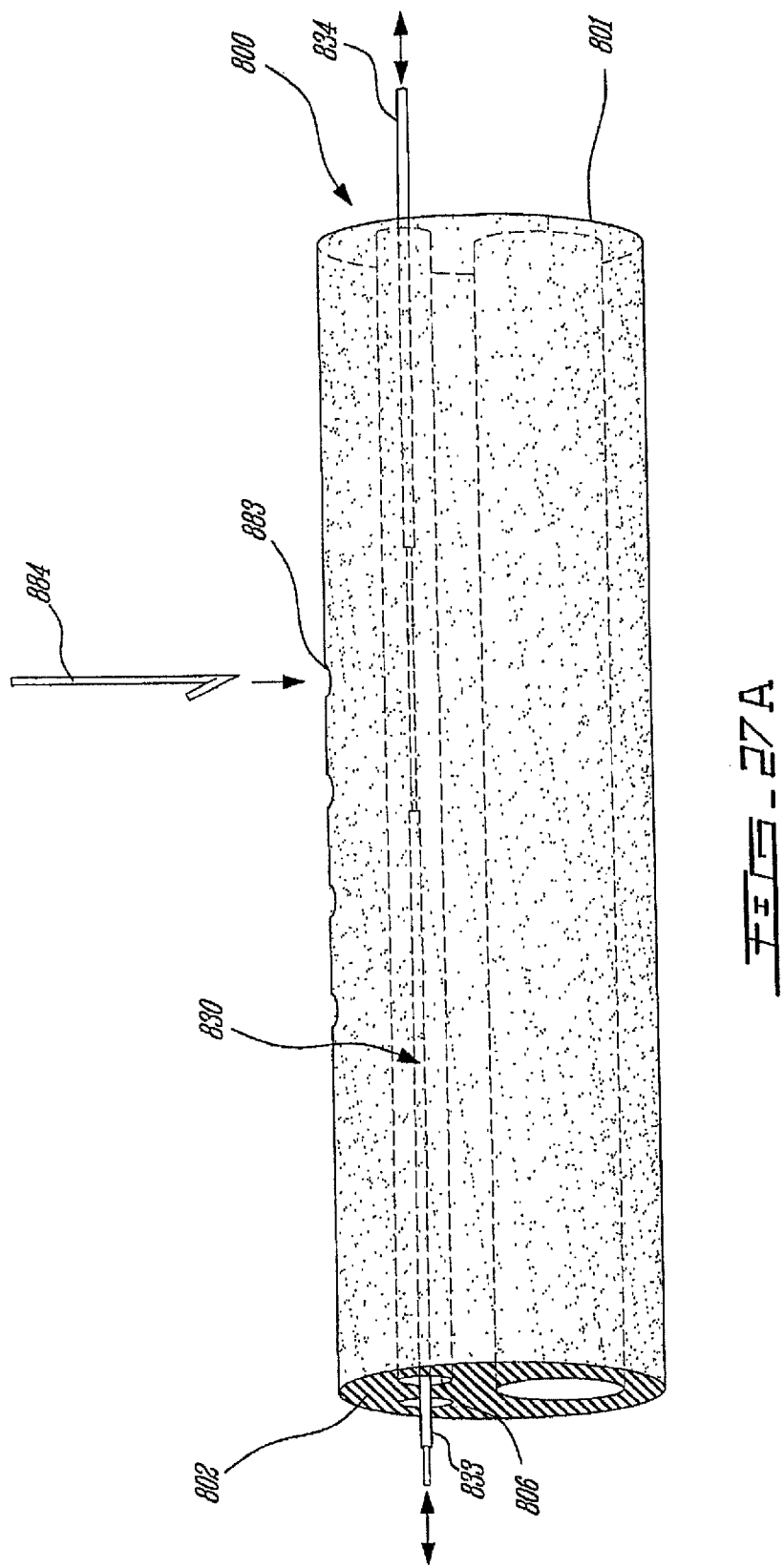
FIGS. 27a and 27b illustrate a method for producing electrode loops with the use of a compressing braid.

There are a number of ways to produce said loops without diverting from the inventive concept of using a compressing braid. An embodiment is disclosed in FIGS. 27a and 27b. For the sake of clarity only one unbraided wire is shown. In FIG. 27a, the wire bundle is in position in the lumen 806 and the hook is dismantled from the braid, thereby lessening the compression force to a minimum. In practice, the compression force will be close to zero. It is now possible to position the individual wire 830 in the lumen 806 by pulling the wire at its proximal and distal ends 833, 834. The insulation of the wire can be readily peeled using any suitable method as shown in FIG. 27a, or the coating can be removed afterwards as discussed previously in relation to FIG. 2. It is to be noted that only a length corresponding to the circumference of the catheter is peeled off the wire, thus leaving the distal end 834 of the wire coated to avoid short circuiting problems.

Figure 20:
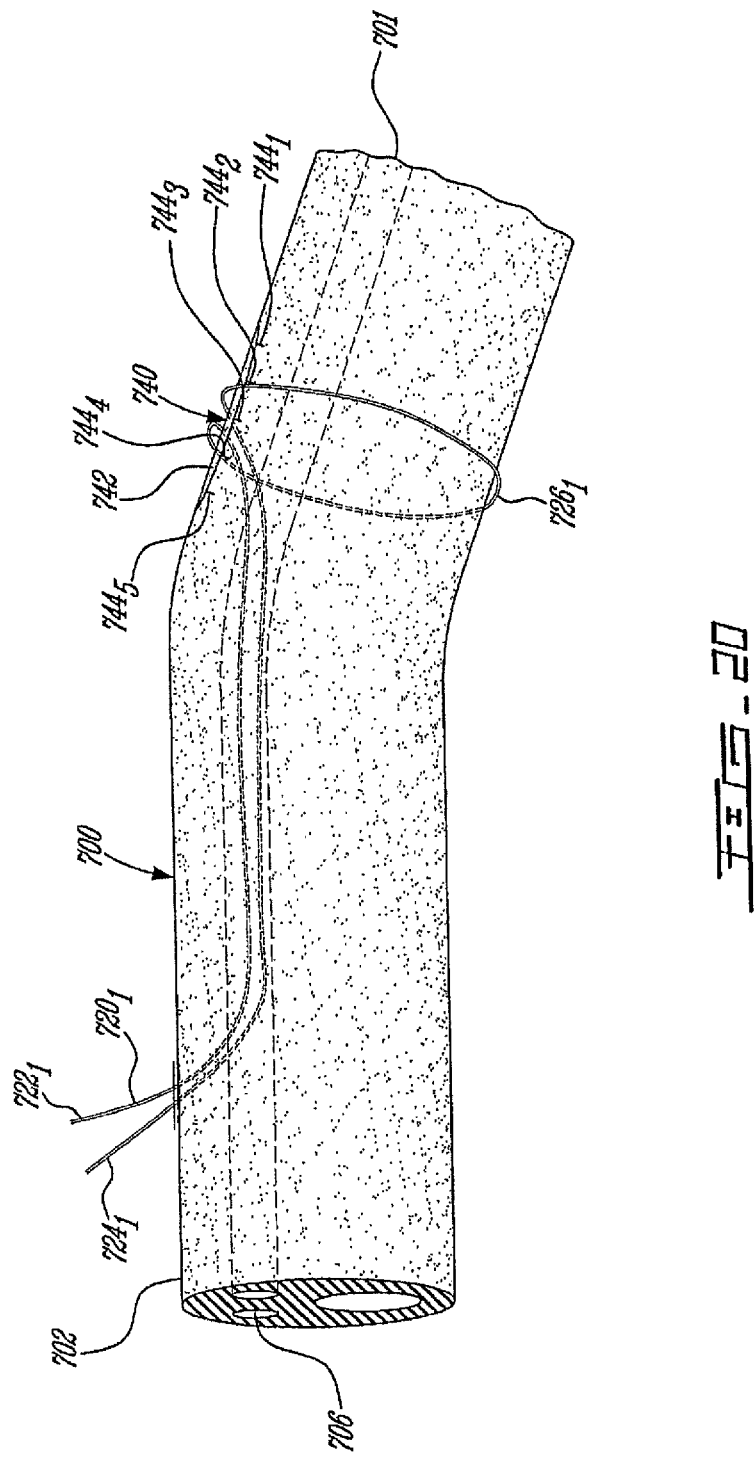
FIG. 20 is a partial cross-sectional view of a thin-wire electrode inside the catheter tubing, the thin-wire electrode having a loop portion that is wound around the exterior wall of the catheter tubing.
Figures 21A, 21B:
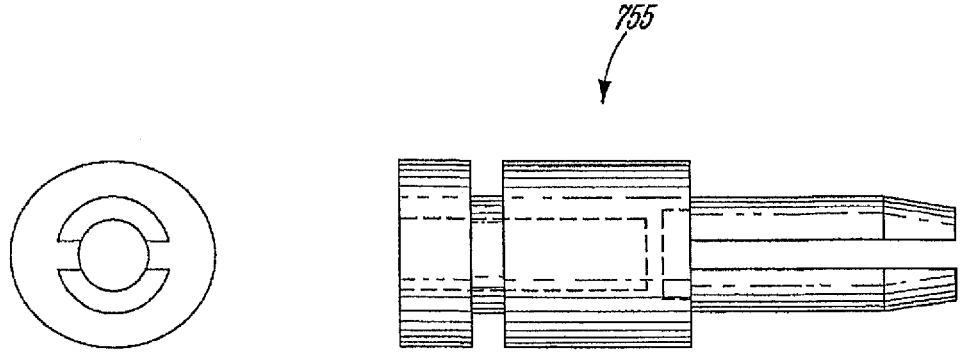
FIG. 21 is a combination front (FIG. 21a) and side (FIG. 21b) views of a slitted female contact pin.
Figure 22:
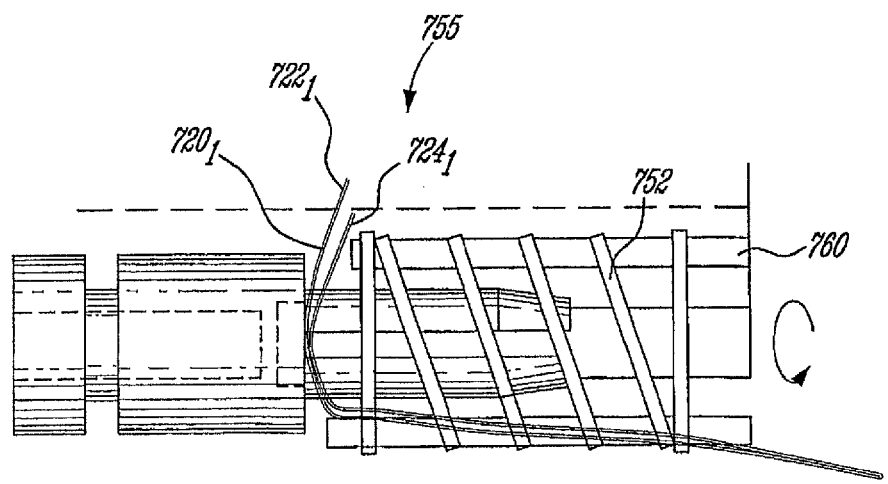
FIG. 22 is a side view of a thin-wire electrode being wrapped around the slitted female contact pin of FIGS. 21a and 21b using a wrapping tool.
Figure 27B:
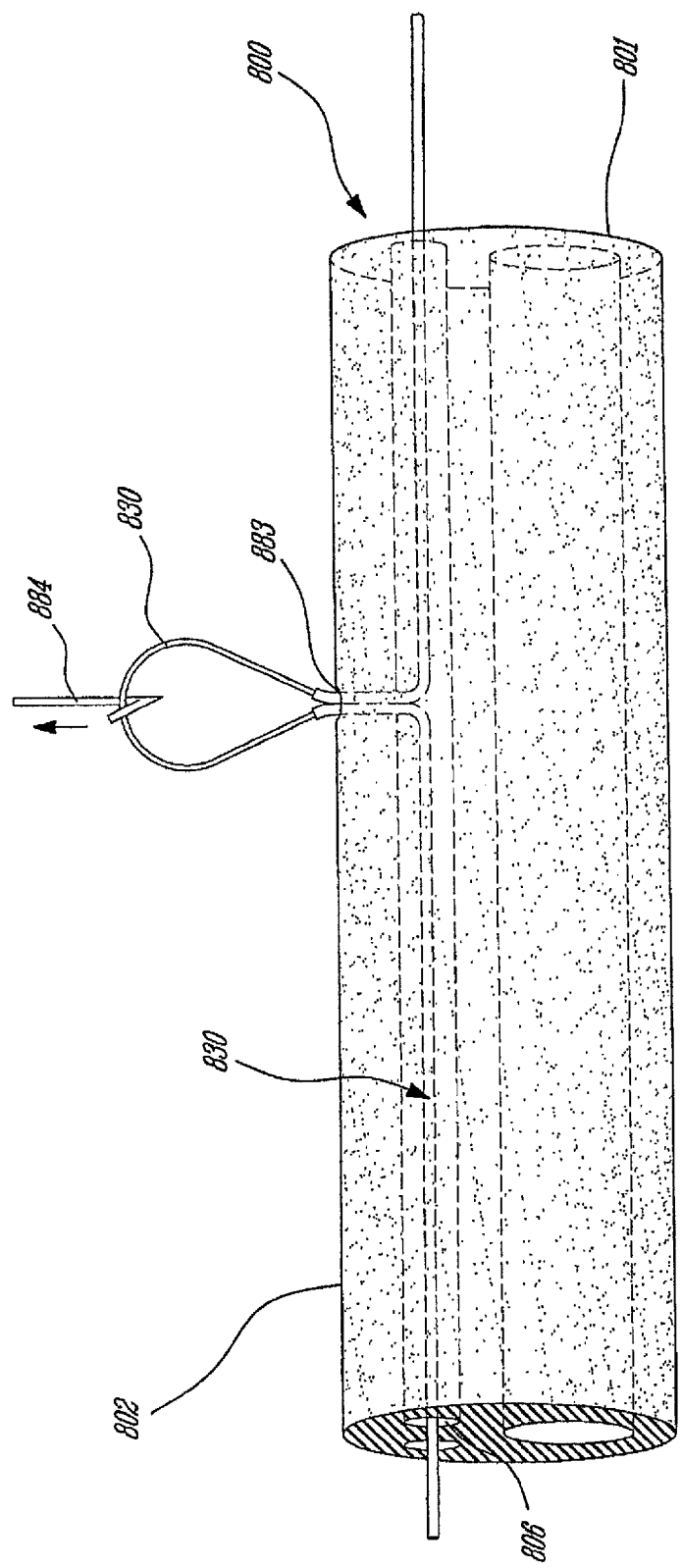

A piercing needle 884 with a hook can be used to pierce the outer wall of the catheter. The catheter may be marked with a series of dots 883 to indicate the locations of the electrodes, and the needle 884 is pulled out of the catheter having the wire 830 on the hook, as shown in FIG. 27b. A sufficient length of the wire is pulled out of the catheter to position the loop around the catheter close to the distal end 801, and the electrode wire loop will position itself when the wire is pulled into the catheter in a manner similar to what is shown in FIGS. 19 and 20. The procedure is repeated for each individual wire 830 to produce the electrodes. The braid can be left inside the catheter or removed prior to the electric connection of the wire at its proximal end 833.

The holes that were made in the catheter during the process of bringing the braided wire bundle into the catheter to make the electrodes are sealed by any suitable method. Such methods are within the purview of those of ordinary skill in the art.

As previously stated, other methods using the braid technique may be used and will be discussed briefly.

A possible method is to follow the procedure disclosed in FIGS. 27a and 27b but the distal end 834 is peeled completely prior to inserting the wires into the catheter. This simplifies the method used to peel the wire from its insulation, since no chemicals need to be used. In this case, the catheter is provided with a small rip at each electrode position. This can be done prior to the piercing of the catheter. Instead of bringing out a loop, the entire uncovered distal end 884 is brought out, wound around the catheter and either fused, tied or knitted in the rip to enhance the positioning of the electrode loop. The holes and rips are sealed, as previously described.

Another method is to provide the braided wires with ready-made loops. For example, the method shown in FIGS. 14 to 20 may be performed in reverse with a braided wire bundle pulled into a slit 42 and each wire loop positioned in a rip 44 defining an electrode position.

EXAMPLE 4

Yet another alternative to the above described embodiments comprises the following electrical modification in respect of an EMG catheter.

In catheters using multiple electrode arrangements for measuring, for example, EMG signals, a common problem is disturbances caused by tribo-electric charging. This effect occurs in four instances:

1. Surface contact effects (friction on the molecular level resulting in chemical bonds that leave imbalanced charges as the surfaces separate and make contact);
2. Work function (material ability to hold onto its free electrons);
3. Charge back flow (two materials that are charged from the above mechanisms and then separated); and
4. Gas breakdown (due to surface topology with microscopic peaks and valleys, charges on the peaks cause corona discharge moving charges through the plasma to the other material).

In the embodiments of the present invention, the braided wires have been pulled through a catheter lumen. The lumen size must therefore be slightly larger than the total diameter of the braided wires because of the pulling tool and in order to adjust the wires. When the ready-made catheter is moved, the wires inside the lumen will scratch against each other and to the wall of the lumen. Then, the triboelectric charges give a disturbance because of the high impedance in the body contact. These movements in the catheter occur when the catheter is inserted into a patient and the patient moves while breathing, etc. In other words, a small charge in high impedance of the system can result in a relatively high output voltage, a noise signal. This is a negative effect, particularly if the patient is being treated for a severe condition, and a consequence could be that the equipment connected to the catheter detects a false pulse and trigger the ventilator in an unwanted way, resulting in a less effective therapy.

To overcome the above problem and minimize the triboelectric effect, the material should be carefully selected. Different plastic material combinations will have higher triboelectric charges than others. However, by inserting materials that discharge and prevent charges to occur, the choice of insulators may be made less critically.

Figure 28A:
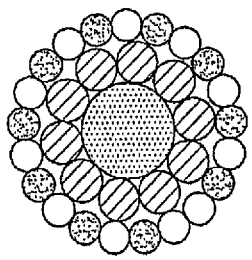
FIG. 28 illustrates conducting braids made from stainless steel wires with a cotton core (FIG. 28a) and without a cotton core (FIG. 28b)

An alternative is to introduce conducting materials in the braid. In FIG. 28a, carbon coal fiber is used in the braid. A positive side effect apart from leveling out induced charges is that the braid may also be used as a capacitive screen to prevent main disturbances from reaching the wires. Any conducting or semi-conducting material can be considered, such as metals, conducting polymers, etc.

In one embodiment, a stabilizing cotton core is introduced in the wire bundle, as illustrated in FIG. 28a. The core will keep the thin steel wires in place and evenly distributed around the core. Thus, the insulation of the wires will be subject to an even distribution of movement and a more equal distribution of charges. Cotton is a neutral material that does not cause charges. Dissipating materials may further remove charges so that they do not reach the electrodes.

Figure 28B:
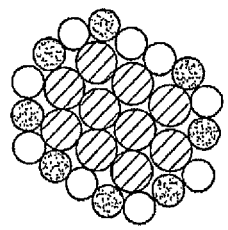

In yet another alternate embodiment shown in FIG. 28b, a conducting braid as described above is used. It is similar to the embodiment shown in FIG. 28a, but differs by not having a cotton core. The electrical properties will not be as good but will be sufficient. On the other hand, a smaller lumen can be used, and thus the diameter of the catheter will be smaller. This may be an important feature to take into account when making catheters intended for infant use.

Furthermore, a possible embodiment is a configuration with a cotton core as in FIG. 28a but with the difference in having bare wires without insulation alternating with insulating dummy wires in-between every conductor to overcome short circuiting problems. This would also require a braid made of a dissipating material, meaning that the conductivity is less than the conductivity of a semiconductor but better than an insulator to transport induced charges. The advantage would be that no peeling of the wires to make the electrode loops are necessary, chemically or mechanically, but the trade off is that twice as many wires has to be configured around the cotton core.

EXAMPLE 5

Figure 29:
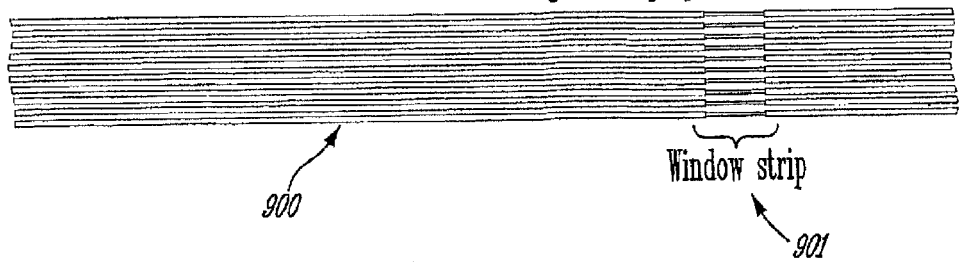
FIG. 29 illustrates ten Stainless Steel 44A WG wires cut to length and prepared for window strip.
Figure 30:
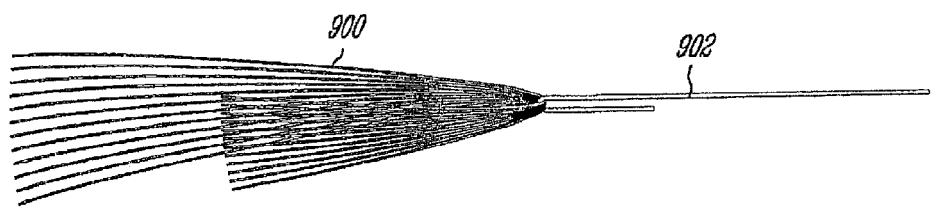
FIG. 30 shows the ten wires of FIG. 29 hooked onto a guide wire to pass the wires through the hollow core of a 0 US silk leaving the window strip portion of the wires exposed at the distal end of the silk.
Figure 31:
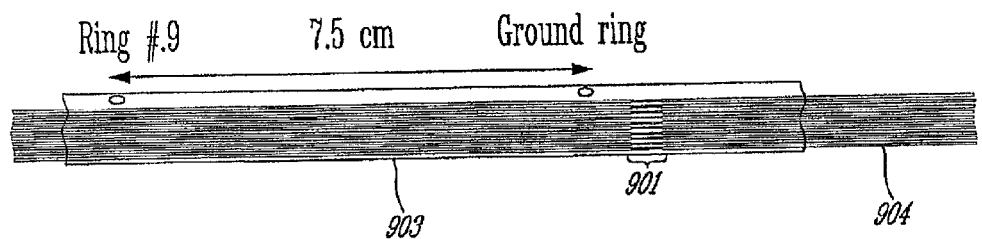
FIG. 31 is a side elevational view showing the wires of FIG. 29 passed through the wire lumen from the distal end to the proximal end of a specially designed polyurethane tube.

An additional example is given with reference to FIGS. 29-34. In this example, the following operation are conducted:
1. Referring to FIG. 29, ten Stainless Steel 44A WG wires 900 are cut to length and prepared for window strip (see 901).
2. Referring to FIG. 30, the ten wires 900 are hooked onto a guide wire 902 and passed through the hollow core of a 0 US silk leaving the window strip portion of the wires exposed at the distal end of the silk.
3. Referring to FIG. 31, the silk 904 containing the wires 900 is hooked to a guide wire and passed through the wire lumen from the distal end to the proximal end of a specially designed polyurethane tube 903.
4. Referring to FIG. 31, the window strip portion 901 is positioned 1 cm distal of the ground ring location.
5. Referring to FIG. 32, a small puncture 905 is made at the marked location of the Ground Ring with the sharp tip of a forcep, a single wire 900 is fished out and the window strip 901 is exposed forming a small loop 906.
6. Referring to FIG. 33, the proximal tip 907 of the tube is carefully passed through the loop 906 formed by the wire in turn placing the wire around the tubing 903.
7. Referring to FIG. 34, both ends of the wire 900 are pulled until the loop 906 is tightened snugly around the tube 903 insuring that the window stripped portion 901 of the wire is fully exposed on the outside of the tube 903.
8. These above operation 107 are repeated for each remaining ring.

Although the present invention has been described by way of illustrative embodiments and examples thereof, it should be noted that it will be apparent to those or ordinary skill in the art that modifications may be applied to the present particular embodiment without departing from the scope of the present invention.

What is claimed is:

1. An electrode assembly, comprising:
an elongated electrode support defining an outer surface, an inner longitudinal conduit, and a wall separating the outer surface and the inner conduit;
at least one ring-type electrode having a loop portion and a wire portion, wherein the loop portion and the wire portion are both made of a same continuous wire having first and second ends; and
a junction of the first end and of a section of the wire spaced apart from the first end;
wherein the wire portion comprises the wire between the junction and the second end;
wherein the loop portion encircles the outer surface generally perpendicular to the elongated electrode support, the wire extends across the wall of the elongated electrode support, and the wire portion extends inside the inner conduit; and
wherein the junction is beneath the outer surface.

2. An electrode assembly as defined in claim 1, wherein the first end of the wire is fused to the section of the wire to form the junction.

3. An electrode assembly as defined in claim 1, wherein the wire is made of a material selected from the group consisting of:
platinum, gold, titanium, silver, silver chloride and stainless steel.

4. An electrode assembly as defined in claim 1, wherein the wire has a thickness ranging from about $10^{-6}$ m to about $10^{-4}$ m.

5. An electrode assembly as defined in claim 1, wherein the loop portion and the wire portion of the ring-type electrode comprises a protective coating.

6. An electrode assembly as defined in claim 1, wherein the at least one ring-type electrode comprises a series of ring-type electrodes, and wherein the electrode assembly further comprises a coating on the loop portions of the ring-type electrodes to control resistivity between successive pairs of laterally adjacent ring-type electrodes of the series.

7. An electrode assembly as defined in claim 1, further comprising a motion-artifact-reducing interface applied to the loop portion of the at least one ring-type electrode to prevent direct contact between tissues of a living body and the loop portion of the at least one ring-type electrode.

8. An electrode catheter, comprising:
- an elongated tubular body defining an outer surface, an inner longitudinal lumen, and a wall separating the outer surface and the lumen;
- an electrode assembly including at least one ring-type electrode having a loop portion and a wire portion, wherein the loop portion and the wire portion are both made of a same continuous wire having first and second ends; and
- a junction of the first end and of a section of the wire spaced apart from the first end;
- wherein the wire portion comprises the wire between the junction and the second end;
- wherein the loop portion encircles the outer surface generally perpendicular to the elongated tubular body, the wire extends across the wall of the elongated tubular body, and the wire portion extends inside the lumen; and
- wherein the junction is beneath the outer surface.

9. An electrode catheter as defined in claim 8, wherein the first end of the wire is fused to the section of the wire to form the junction.

10. An electrode catheter as defined in claim 8, wherein the wire is made of a material selected from the group consisting of:
- platinum, gold, titanium, silver, silver chloride and stainless steel.

11. An electrode catheter as defined in claim 8, wherein the wire has a thickness ranging from about $10^{-6}$ m to about $10^{-4}$ m.

12. An electrode catheter as defined in claim 8, wherein the loop portion and the wire portion of the ring-type electrode comprises a protective coating.

13. An electrode catheter as defined in claim 8, wherein the at least one ring-type electrode comprises a series of ring-type electrodes, and wherein the electrode assembly further comprises a coating on the loop portions of the ring-type electrodes to control resistivity between successive pairs of laterally adjacent ring-type electrodes of the series.

14. An electrode catheter as defined in claim 8, further comprising a motion-artifact-reducing interface applied to the loop portion of the at least one ring-type electrode to prevent direct contact between tissues of a living body and the loop portion of the at least one ring-type electrode.

15. An electrode device for a host tube with longitudinal, lateral implement-receiving means, comprising:
- an electrode assembly comprising at least one ring-type electrode having a loop portion and a wire portion; and
- an elongated electrode support structured to be mounted in the longitudinal, lateral implement-receiving means on one side of the host tube, the elongated electrode support having at least one transversal indent through which the loop portion of the at least one ring-type electrode is mounted on the elongated electrode support and a longitudinal, inner groove in the elongated electrode support and in communication with the at least one transversal indent;
- wherein, when the elongated electrode support is mounted in the longitudinal, lateral implement-receiving means on one side of the host tube, the longitudinal inner groove forms with a surface of the host tube a longitudinal conduit in which the wire portion of the at least one ring-type electrode is placed to extend along the elongated electrode support and the host tube.

16. An electrode device as defined in claim 15, wherein the at least one ring-type electrode comprises a plurality of ring-type electrodes each with a loop portion and a wire portion, and wherein the at least one transversal indent comprises a series of transversal indents to receive the loop portions of the plurality of ring-type electrodes of the electrode assembly.

17. An electrode assembly, comprising:
- at least one ring-type electrode having a loop portion and a wire portion;
- a host tube with longitudinal, lateral implement-receiving means; and
- an elongated electrode support mounted in the longitudinal, lateral implement-receiving means on one side of the host tube, the elongated electrode support having at least one transversal indent through which the loop portion of the at least one ring-type electrode is mounted on the elongated electrode support and a longitudinal, inner groove in the elongated electrode support and in communication with the at least one transversal indent;
- wherein the longitudinal inner groove forms with a surface of the host tube a longitudinal conduit in which the wire portion of the at least one ring-type electrode is placed to extend along the elongated electrode support and the host tube.

18. An electrode assembly as defined in claim 17, wherein the longitudinal, lateral implement-receiving means comprises a longitudinal groove.

19. An electrode assembly as defined in claim 18, wherein the elongated electrode support and the longitudinal groove have transversal, complementary cross sections shaped to allow the elongated electrode support to clip into the longitudinal groove.

* * * * *